(12) United States Patent
Civelli et al.

(10) Patent No.: US 6,203,998 B1
(45) Date of Patent: Mar. 20, 2001

(54) HUMAN DOPAMINE RECEPTOR AND ITS USES

(75) Inventors: Olivier Civelli, Aesch (CH); Hubert Henri-Marie Van Tol, Toronto (CA)

(73) Assignee: Oregon Health Sciences Univ., Portland, OR (US)

( * ) Notice: Subject to any disclaimer, the term of this patent is extended or adjusted under 35 U.S.C. 154(b) by 0 days.

(21) Appl. No.: 09/060,694

(22) Filed: Apr. 15, 1998

Related U.S. Application Data

(62) Division of application No. 08/487,811, filed on Jun. 7, 1995, now Pat. No. 5,883,226, which is a division of application No. 07/928,611, filed on Aug. 10, 1992, now Pat. No. 5,569,601, which is a continuation-in-part of application No. 07/626,618, filed on Dec. 7, 1990, now Pat. No. 5,422,265.

(51) Int. Cl.[7] .................. G01N 33/53; G01N 33/567; C12N 5/10
(52) U.S. Cl. .................. 435/7.21; 435/7.1; 435/7.2; 436/501
(58) Field of Search ................ 435/6, 7.1, 7.2, 435/7.21, 69.1, 69.7; 436/501; 536/23.5, 23.4

(56) References Cited

U.S. PATENT DOCUMENTS

| | | |
|---|---|---|
| 4,599,308 | 7/1986 | Hamer . |
| 4,650,764 | 3/1987 | Temin . |
| 4,683,195 | 7/1987 | Mullis . |
| 4,683,202 | 7/1987 | Mullis . |
| 4,761,371 | 8/1988 | Bell . |
| 4,861,719 | 8/1989 | Miller . |
| 5,422,265 | 6/1995 | Civelli . |
| 5,569,601 | 10/1996 | Civelli . |

FOREIGN PATENT DOCUMENTS

| | | |
|---|---|---|
| WO 91/12339 | 8/1991 | (WO) . |
| WO 92/10571 | 6/1992 | (WO) . |
| WO 94/03602 | 2/1994 | (WO) . |

OTHER PUBLICATIONS

Ackenheil et al., "Antiphsychotische Wirksamkeit im Verhaltiszum Plamaspiegal von Clozapin," Arzneim–Forsch 26, 1156–1158 (1976).
Amlaiky and Caron, "Identification of the D2–Dopmine Receptor Binding Subunit in Several Mammalian Tissues and Species by Photaffinity Labeling," J. Neurochem. 47, 196–204 (1986).
Amlaiky and Caron, "Photoaffinity Labeling of the D2–dopamine Receptor Using a Novel High Affinity Radioiodinated Probe," J. Biol Chem. 260, 1983–1986 (1985).
Amlaiky et al., "Identification of the Binding Subunit of the D1–Dopamine Receptor by Photoaffinity Crossliking," Mol. Pharmacol. 31, 129–134 (1987).
Bertling, "Transfection of a DNA/Protein Complex into Nuclei of Mammalian Cells Using Polyoma Capsides and Electroporation," Bioscience Reports 7, 107112 (1987).
Botstein et al., "Construction of a Genetic Linkage Map in Man Using Restriction fragment Length Polymorphisms," Am. J. Hum. Genet. 32, 314–331 (1980).
Bouvier et al., "Removal of phosphorylation sites from the b2–adrenergic receptor delays onset of agonist–promoted desensitization," Nature 333, 370–373 (1988).
Bunzow et al., "Cloning and expression of a rat D2 dopamine receptor cDNA," Nature 336, 783–787 (1988).
Casey, "Clozapine: neuroleptic–induced EPS and tardive dyskinesia," Psychopharmacology 99, S47–S53 (1989).
Cooper et al., "Catecholamines II: CNS Aspects," in The Biochemical Basis of Neuropharmacology, 3d ed. 1978 (Oxford University Press, N.Y.), pp. 161–195.
Dal Toso et al. EMBO J. 8, 4025–4034 (1989).
Young and Davis, "Efficient isolation of genes by using antibody probes," Proc. Natl. Acad. Sci. USA 80, 1194–1198 (1983).
Dohlman et al., Biochemistry 26, 2657–2664 (1987).
Fiers et al., "Complete nucleotide sequence of SV40 DNA," Nature 273, 113 (1978).
Gingrich et al., J Biochemistry 27, 3907–3912 (1988).
Gorman et al., "High Efficiency DNA–Mediated Transformation of Primate Cells," Science 221, 551–553 (1983).
Grandy et al., "Cloning of the cDNA and gene for a human D2 dopamine receptor," Proc. Natl. Acad. Sci. USA 86, 9762–9766 (1989).
Hubbard & Ivatt, "Synthesis and Processing of Asparagine–Linked Oligosaccharides 1.2," Ann. Rev. Biochem 50, 555–583 (1981).
Jarvie et al., "Dopamine D2 Receptor Binding Subunits of Mr @ 140,000 and 94,000 in Brain: Deglycosylation Yields a Common Unit of Mr @ 44,000," Mol. Pharmacol. 34, 91–97 (1988).
Kane et al., "Clozapine for the Treatment–Resistant Schizophrenic," Arch. Gen. Psychiat. 45, 789–796 (1988).
Kebabian and Calne, "Multiple receptors for dopamine," Nature 277, 93–96 (1979).
Kennedy et al., "A HincII RFLP in the human D4 dopamine receptor locus (DRD4)," Nucleic Acids Research 19(20), 5801 (1991).

(List continued on next page.)

Primary Examiner—John Ulm
(74) Attorney, Agent, or Firm—McDonnell Boehnen Hulbert & Berghoff

(57) ABSTRACT

The present invention is directed toward isolation, characterization and pharmacological use of the human D4 dopamine receptor. The nucleotide sequence of the gene corresponding to this receptor and alleleic variant thereof are provided by the invention. The invention also includes recombinant eukaryotic expression constructs capable of expressing the human D4 dopamine receptor in cultures of transformed eukaryotic cells. The invention provides cultures of transformed eukaryotic cells which synthesize the human D4 dopamine receptor, and methods for characterizing novel psychotropic compounds using such cultures.

12 Claims, 20 Drawing Sheets

OTHER PUBLICATIONS

Kozak, "Compliation and analysis of sequences upstream from the translation start site in eukaryotic mRNAs," Nucleic Acids Res. 12, 857–872 (1984).

Mount, "A catalogue of splice junction sequences," Nucl. Acids. Res. 10, 461–472 (1982).

Mullis, "The Polymerase Chain Reaction: Why It Works," in Curr. Commun. Mol. Bio., Polymerase Chain Reaction, Erlich, Gibbs & Kazazian, eds., Cold Springs Harbor Press, pp. 237–243 (1987).

Ninik et al., Biochemistry 27, 7594–7599 (1988).

Noonan et al., "Quantitative Estimation of MDR1 mRNA Levels by Polymerase Chain Reaction," in Molecular and Cellular Biology of Multidrug Resistance in Tumor Cells, Roninson eds., Plenum Publishing Corporation, 1991, pp. 319–333.

O'Dowd et al., "Palmitoylation of the Human b2–Adrenergic Receptor," J. Biol. Chem. 264, 7564–7569 (1989).

"Quantitative Filter Hybridization: 5.1 Discrimination between related sequences–stringency of hybridization," 1985, in Nucleic Acid Hybridisation: A Practical Approach, Hames & Higgins, eds., IRL Press, pp. 81–82.

Sanger et al., "DNA sequencing with chain–terminating inhibitors," Proc. Natl. Acad. Sci. USA 74 (12), 5463–5467 (1977).

Seeman et al., "Human Brain D1 and D2 Dopamine Receptor in Schizophrenia, Alzheimer's, Parkinson's and Huntington's Diseases," Neuropshchopharm. 1,5–15 (1987).

Seeman, Synapse 1, 133–152 (1987).

Sengoles et al., "Purification and Characterization of the D2–Dopamine Receptor from Bovine Anterior Pituitary," J. Biol. Chem. 263, 18996–19002 (1988).

Senogles et al., Biochemistry 25, 749–753 (1986).

Sibley et al., Cell 48, 913–922 (1987).

Smithies et al., "Insertion of DNA sequences into the human chromosomal b–globin locus by homologous recombination," Nature 317, 230–234 (1985).

Sokoloff et al., "Molecular cloning and characterization of a novel dopamine receptor (D3) as a target for neuroleptics," Nature 347, 146–151 (1990).

Sokoloff et al., "Pharmacology of human dopamine D3 receptor expressed in a mammalian cell line: comparison with D2 receptor," European Journal of Pharmacology 225, 331–337 (1992).

Sommer et al., "Minimal homology requirements for PCR primers," Nucleic Acids Research 17(16), 6749 (1989).

Strader et al., "Conserved Aspartic Acid Residues 79 and 113 of the b–Adrenergic Receptor Have Different Roles in Receptor Function," J. Biol. Chem. 263, 10267–19271 (1988).

Sunahara et al., "Human dopamine D1 receptor encoded by an intronless gene on chromosome 5," Nature 347, 80–83 (1990).

Thomas & Capecchi, "Site–Directed Mutagenesis by Gene Targeting in Mouse Embryo–Derived Stem Cells," Cell 51, 503–512 (1987).

Urwyler et al., "Identification of dopamine D3 and D4 binding sites, labeled with [3H]2–amino–6,7–dihy droxy–1,2,3,4–tetrahydronaphthalene, as high agonist affinity states of the D1 and D2 dopamine receptors, respectively," Journal of Neurochemistry 46(4), 1058–1067 (1986).

Van Tol et al., "Cloning of the gene for a human dopamine D4 receptor with high affinity for the antipsychotic clozapine," Nature 350, 610–614 (1991).

Van Tol et al., "Multiple Dopamine D4 Receptor Variants in the Human Population," Nature 358, 149–152 (1992).

Zhou et al., "Cloning and expression of human and rat D1 dopamine receptors," Nature 347, 76–80 (1990).

Zubay, "The Building Blocks of Proteins: Amino Acids, Peptides, and Polypeptides," Biochemistry (2d. ed.), 1988 (MacMillen Publishing, NY) p. 33).

Figure 2A

```
5'-CGGGGGCGGGACCAGGGTCCGGCCGGGGCGTGCCCCC
GGGGAGGGACTCCCCGGCTTGCCCCCGGCGTTGTCCGCGGTG
                           +1
CTCAGCGCCCGCCCGGGCGCGCC ATG GGG AAC CGC AGC
                        MET GLY ASN ARG SER
                                            48
ACC GCG GAC GCG GAC GGG CTG CTG GCT GGG CGC
THR ALA ASP ALA ASP GLY LEU LEU ALA GLY ARG
                                 ▲
GGG CGG GCC GCG GGG GCA TCT GCG GGG GCA TCT
GLY PRO ALA ALA GLY ALA SER ALA GLY ALA SER
                                            114
GCG GGG CTG GCT GGG CAG GGC GCG GCG GCG CTG
ALA GLY LEU ALA GLY GLN GLY ALA ALA ALA LEU

GTG GGG GGC GTG CTG CTC ATC GGC GCG GTG CTC
VAL GLY GLY VAL LEU LEU ILE GLY ALA VAL LEU
                                            180
GCG GGG AAC TCG CTC GTG TGC GTG AGC GTG GCC
ALA GLY ASN SER LEU VAL CYS VAL SER VAL ALA

ACC GAG CGC GCC CTG CAG ACG CCC ACC AAC TCC
THR GLU ARG ALA LEU GLN THR PRO THR ASN SER
                                            246
TTC ATC GTG AGC CTG GCG GCC GCC GAC CTC CTC
PHE ILE VAL SER LEU ALA ALA ALA ASP LEU LEU

CTC GCT CTC CTG GTG CTG CCG CTC TTC GTC TAC
LEU ALA LEU LEU VAL LEU PRO LEU PHE VAL TYR

TCC GAG GTGAGCCGCGTCCGGCCGCA...............
SER GLU

...CCTGTGGTGTCGCCGCGCAG GTC CAG GGT GGC GCG
                        VAL GLN GLY GLY ALA
                                            333
TGG CTG CTG AGC CCC CGC CTG TGC GAC GCC CTC
TRP LEU LEU SER PRO ARG LEU CYS ASP ALA LEU
```

Figure 2B

```
ATG GCC ATG GAC GTC ATG CTG TGC ACC GCC TCC
MET ALA MET ASP VAL MET LEU CYS THR ALA SER
                                              398
ATC TTC AAC CTG TGC GCC ATC AGC GTG GAC AG
ILE PHE ASN LEU CYS ALA ILE SER VAL ASP ARG

GTGCGCCGCCCTCCCCGCCCGCGCCCCGGCGCCCCCGCGCCCC

GCCCGCCGCCCTCACCGCGGCCTGTGCGCTGTCCGGCGCCCCC

TCGGCGCTCCCCGCAG   G TTC GTG GCC GTG GCC GTG
                     PHE VAL ALA VAL ALA VAL
                                              450
CCG CTG CGC TAC AAC CGG CAG GGT GGG AGC CGC
PRO LEU ARG TYR ASN ARG GLN GLY GLY SER ARG

CGG CAG CTG CTG CTC ARC GGC GCC ACG TGG CTG
ARG GLN LEU LEU LEU ILE GLY ALA THR TRP LEU
                                          □ 516
CTG TCC GCG GCG GTG GCG GCG CCC GTA CTG TGC
LEU SER ALA ALA VAL ALA ALA PRO VAL LEU CYS

GGC CTC AAC GAC GTG CGC GGC CGC GAC CCC GCC
GLY LEU ASN ASP VAL ARG GLY ARG ASP PRO ALA
                                             582
GTG TGC CGC CTG GAG GAC CGC GAC TAC GTG GTC
VAL CYS ARG LEU GLU ASP ARG ASP TYR VAL VAL

TAC TCG TCC GTG TGC TCC TTC TTC CTA CCC TGC
TYR SER SER VAL CYS SER PHE PHE LEU PRO CYS
                                             648
CCG CTC ATG CTG CTG CTG TAC TGG GCC ACG TTC
PRO LEU MET LEU LEU LEU TYR TRP ALA THR PHE

CGC GGC CTG CAG CGC TGG GAG GTG GCA CGT CGC
ARG GLY LEU GLN ARG TRP GLU VAL ALA ARG ARG
                                             714
GCC AAG CTG CAC GGC CGC GCG CCC CGC CGA CCC
ALA LYS LEU HIS GLY ARG ALA PRO ARG ARG PRO
```

Figure 2C

```
AGC GGC CCT GGC CCG CCT TCC CCC ACG CCA CCC
SER GLY PRO GLY PRO PRO SER PRO THR PRO PRO
                                            780
GCG CCC CGC CTC CCC CAG GAC CCC TGC GGC CCC
ALA PRO ARG LEU PRO GLN ASP PRO CYS GLY PRO
 ■
GAC TGT GCG CCC CCC GCG CCC GGC CT TCCCCGGG
ASP CYS ALA PRO PRO ALA PRO GLY LEU

GTCCCTGCGGCC......CCTGTGCGCCCCCGCGCCCGGCCT

CCCCCAGGACCCCTGCGGCCCCGACTGTGCGCCCCCGCGCCC
                                        834
GGCCT C CCC CCG GAC CCC TGC GGC TCC AAC TGT
      PRO PRO ASP PRO CYS GLY SER ASN CYS

GCT CCC CCC GAC GCC GTC AGA GCC GCC GCG CTC
ALA PRO PRO ASP ALA VAL ARG ALA ALA ALA LEU
                                          900
CCA CCC CAG ACT CCA CCG CAG ACC CGC AGG AGG
PRO PRO GLN THR PRO PRO GLN THR ARG ARG ARG

CGG CGT GCC AAG ATC ACC GGC CGG GAG CGC AAG
ARG ARG ALA LYS ILE THR GLY ARG GLU ARG LYS
                                    □
GCC ATG AGG GTC CTG CCG GTG GTG GTC G GTGG
ALA MET ARG VAL LEU PRO VAL VAL VAL
         □
GTTCCTGTCCTGAGGGGCGGGGAGGAGAGGAGGGGGGGAGTAC

GAGGCCGGCTGGGCGGGGGGCGCTAACGCGGCTCTCGGCGCCC

CCAG GG GCC TTC CTG CTG TGC TGG ACG CCC TTC
     GLY ALA PHE LEU LEU CYS TRP THR PRO PHE
                                         1023
TTC GTG GTG CAC ATC ACG CAG GCG CTG TGT CCT
PHE VAL VAL HIS ILE THR GLN ALA LEU CYS PRO
```

Figure 2D

```
GCC TGC TCC GTG CCC CCG CGG CTG GTC AGC GCC
ALA CYS SER VAL PRO PRO ARG LEU VAL SER ALA
                                         1089
GTC ACC TGG CTG GGC TAC GTC AAC AGC GCC CTC
VAL THR TRP LEU GLY TYR VAL ASN SER ALA LEU

ACC CCC GTC ATC TAC ACT GTC TTC AAC GCC GAG
ASN PRO VAL ILE TYR THR VAL PHE ASN ALA GLU
                                         1155
TTC CGC AAC GTC TTC CGC AAG GCC CTG CGT GCC
PHE ARG ASN VAL PHE ARG LYS ALA LEU ARG ALA
    1164
TGC TGC TGA GCCGGGCACCCCCGGACGCCCCCCGGCCTG
CYS CYS STOP

ATGGCCAGGCCTCAGGGACCAAGGAGATGGGGAGGGCGCTTTT

GTACGTTAATTAAACAAATTCCTTCCCAAACTCAGCTGTGAAG
                                 AAAAAAAAAAAAAAAAAA
GCTCCTGGG-3'
AA
```

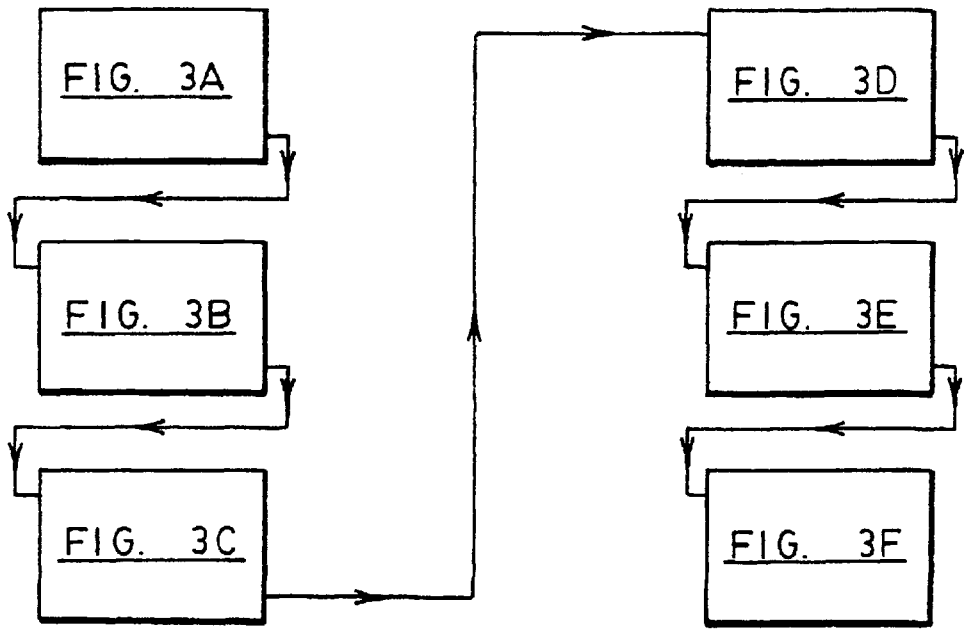

```
D1 HUMAN  P A T N N A I E T V S I N N N G A A M F S S H H E P R G S I S K
D1 RAT    P T T N N A I E T V S I N N N G A V V F S S H H E P R G S I S K

D1 HUMAN  E C N L V Y L I P H A V G S S E D L K K E A A G G I A R P L E K
D1 RAT    D C N L V Y L I P H A V G S S E D L K K E A A G G I A K P L E K

D1 HUMAN  L S P A L S V I L D Y D I D V S L E K I Q P T N G Q H P T
D1 RAT    L S P A L S V I L D Y D I D V S L E K I Q P V T H S Q H S T

D1 HUMAN  446
D1 RAT    446
```

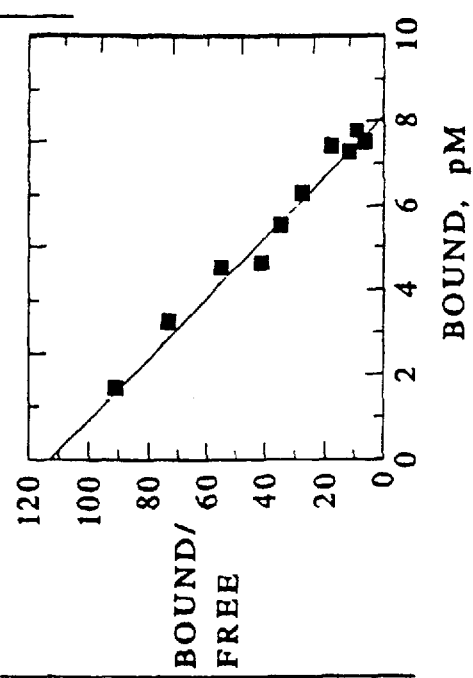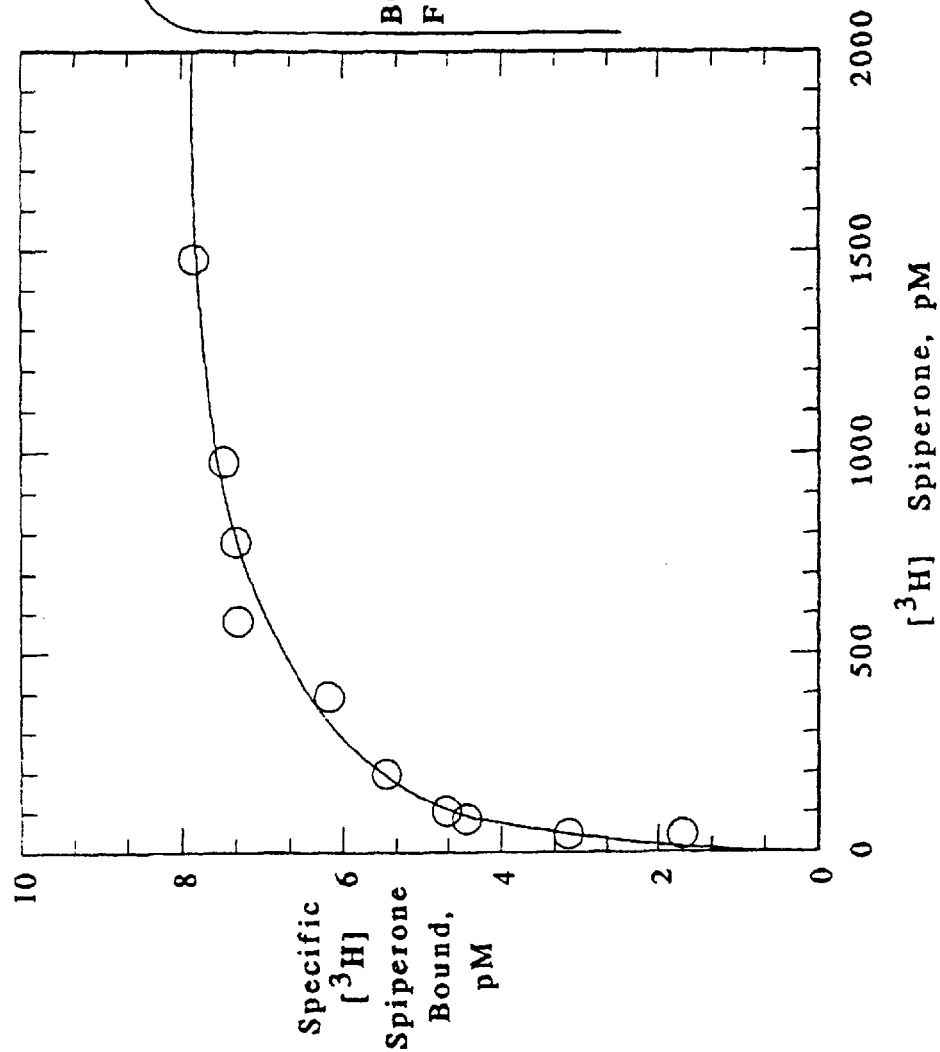

FIG. 6A

```
D4 2...ACG CC A CCC GCG CCC CGC CTC CCC CAG GAC CCC TGC GGC CCC GAC TGT GCG CC
D4 4...ACG CC A CCC GCG CCC CGC CTC CCC CAG GAC CCC TGC GGC CCC GAC TGT GCG CC
D4 7...ACG CC A CCC GCG CCC CGC CTC CCC CAG GAC CCC TGC GGC CCC GAC TGT GCG CC

REPEAT 2      C CCC GCG CCC GGC CTT CCC CGG GGT CCC TGC GGC CCC GAC TGT GCG CC
              C CCC GCG CCC GGC CTT CCC CGG GGT CCC TGC GGC CCC GAC TGT GCG CC

REPEAT 3      C GCC GCG CCC GGC CTC CCC CCG GAC CCC TGC GGC CCC GAC TGT GCG CC

REPEAT 4      C CCC GCG CCC GGC CTC CCC CAG GAC CCC TGC GGC CCC GAC TGT GCG CC

REPEAT 5      C CCC GCG CCC GGC CTT CCC CGG GGT CCC TGC GGC CCC GAC TGT GCG CC

REPEAT 6    C G|CC GCG CCC A|GC CTC CCC CCC CAG GAC CCC TGC GGC TCC AAC TGT GCT CCC CCC...
              C CCC GCG CCC GGC CTC CCC CCC CAG GAC CCC TGC GGC TCC AAC TGT GCT CCC CCC...

REPEAT 7      C CCC GCG CCC GGC CTC CCC CCG GAC CCC TGC GGC TCC AAC TGT GCT CCC CCC...
              C CCC GCG CCC GGC CTC CCC CCG GAC CCC TGC GGC TCC AAC TGT GCT CCC CCC...
```

HUMAN DOPAMINE RECEPTOR AND ITS USES

This application is a divisional of U.S. Ser. No. 08/487,811, filed Jun. 7, 1995, now U.S. Pat. No. 5,883,226, which is a divisional of U.S. Ser. No. 07/928,611, filed Aug. 10, 1992, now U.S. Pat. No. 5,569,601, issued Oct. 29, 1996, which is a continuation-in-part of U.S. Ser. No. 07/626,618, filed Dec. 7, 1990, now U.S. Pat. No. 5,422,265, issued Jun. 6, 1995.

This invention was made with government support under NIMH grant MH-45614 awarded by the National Institutes of Health, Unites States of America, and grant PG 11121 awarded by the Medical Research Council of Canada. The governments have certain rights in the invention.

BACKGROUND OF THE INVENTION

1. Field of the Invention

The invention relates to dopamine receptors from mammalian species and the genes corresponding to such receptors. In particular, it relates to the human dopamine receptor D4. Specifically, the invention relates to the isolation, cloning and sequencing of the human D4 receptor gene. The invention also relates to the construction of eukaryotic expression vectors capable of expression of the human D4 dopamine receptor in cultures of transformed eukaryotic cells and the synthesis of the human D4 dopamine receptor in such cultures. The invention relates to the use of such cultures of transformed eukaryotic cells producing the human D4 dopamine receptor for the characterization of antipsychotic drugs.

2. Information Disclosure Statement

Dopamine is a neurotransmitter that participates in a variety of different functions mediated by the nervous system, including vision, movement, and behavior (see generally Cooper et al., 1978, *The Biochemical Basis of Neuropharmacology*, 3d ed., Oxford University Press, New York, pp 161–195). The diverse physiological actions of dopamine are in turn mediated by its interaction with two of the basic types of G protein-coupled receptors, D1 and D2, which respectively stimulate and inhibit the enzyme adenylyl cyclase (Kebabian & Calne, 1979, Nature 277: 93–96). Alterations in the number or activity of these receptors may be a contributory factor in disease states such as Parkinson's disease (a movement disorder) and schizophrenia (a behavioral disorder).

A great deal of information has accumulated on the biochemistry of the D1 and D2 dopamine receptors, and methods have been developed to solubilize and purify these receptor proteins (see Senogles et al., 1986, Biochemistry 25: 749–753; Sengoles et al., 1988, J. Biol. Chem. 263: 18996–19002; Gingrich et al., 1988, Biochemistry 27: 3907–3912). The D1 dopamine receptor in several tissues appears to be a glycosylated membrane protein of about 72 kD (Amlaiky et al., 1987, Mol. Pharmacol. 31: 129–134; Ninik et al., 1988, Biochemistry 27: 7594–7599). The D2 receptor has been suggested to have a higher molecular weight of about 90–150 kD (Amlaiky & Caron, 1985, J. Biol. Chem. 260: 1983–1986; Amlaiky & Caron, 1986, J. Neurochem. 47: 196–204; Jarvie et al., 1988, Mol. Pharmacol. 34: 91–97). Much less is known about a recently discovered additional dopamine receptor, termed D3 (Sokoloff et al., 1990, Nature 347: 146–151).

Dopamine receptors are primary targets in the clinical treatment of psychomotor disorders such as Parkinson's disease and affective disorders such as schizophrenia (Seeman et al., 1987, Neuropsychopharm. 1: 5–15; Seeman, 1987, Synapse 1: 152–333). The three different dopamine receptors (D1, D2, D3) have been cloned as a result of nucleotide sequence homology which exists between these receptor genes (Bunzow et al., 1988, Nature 336: 783–787; Grandy et al., 1989, Proc. Natl. Acad. Sci. USA 86: 9762–9766; Dal Toso et al., 1989, EMBO J. 8: 4025–4034; Zhou et al., 1990, Nature 346: 76–80; Sunahara et al., 1990, Nature 346: 80–83; Sokoloff et al., 1990, Nature 347: 146–151).

The antipsychotic clozapine is useful for socially withdrawn and treatment-resistant schizophrenics (see Kane et al., 1990, Nature 347: 146–151), but unlike other antipsychotic drugs, clozapine does not cause tardive dyskinesia (see Casey, 1989, Psychopharmacology 99: 547–553). Clozapine, however, has dissociation constants for D2 and D3 which are 3 to 30-fold higher than the therapeutic free concentration of clozapine in plasma water (Ackenheil et al., 1976, Arzneim-Forsch 26: 1156–1158; Sandoz Canada, Inc., 1990, Clozaril: Summary of preclinical and clinical data). This suggests the existence of dopamine receptors more sensitive to the antipsychotic clozapine than those known in the prior art heretofore.

We have cloned and sequenced such a human dopamine receptor which we term D4. The dopamine D4 receptor gene has high homology to the human dopamine D2 and D3 receptor genes. The pharmacological profile of this receptor resembles that of the D2 and D3 receptors but it has an affinity for clozapine which is tenfold higher. The present inventors envision that the D4 dopamine receptor disclosed as this invention may prove useful in discovering new types of drugs for schizophrenia that like clozapine do not induce tardive dyskinesia and other motor side effects.

We have also discovered that the D4 gene is polymorphic in the human population, having at least 7 different alleles that can be detected by restriction fragment length polymorphism analysis (see, Botstein et al., 1980, Am. J. Hum. Genet. 32: 314–331). This is the first receptor in the catecholamine receptor family which displays polymorphic variations in the human population. The observed polymorphism in dopamine D4 receptor genes may underlie individual differences in susceptibility to neuropsychiatric disorders such as schizophrenia and manic depression, as well as responsiveness to antipsychotic medication.

DESCRIPTION OF THE DRAWINGS

FIGS. 2A through 2D illustrates the nucleotide sequence (SEQ ID No. 17) of genomic and cDNA clones of the human D4 dopamine receptor gene.

Figure 3D:
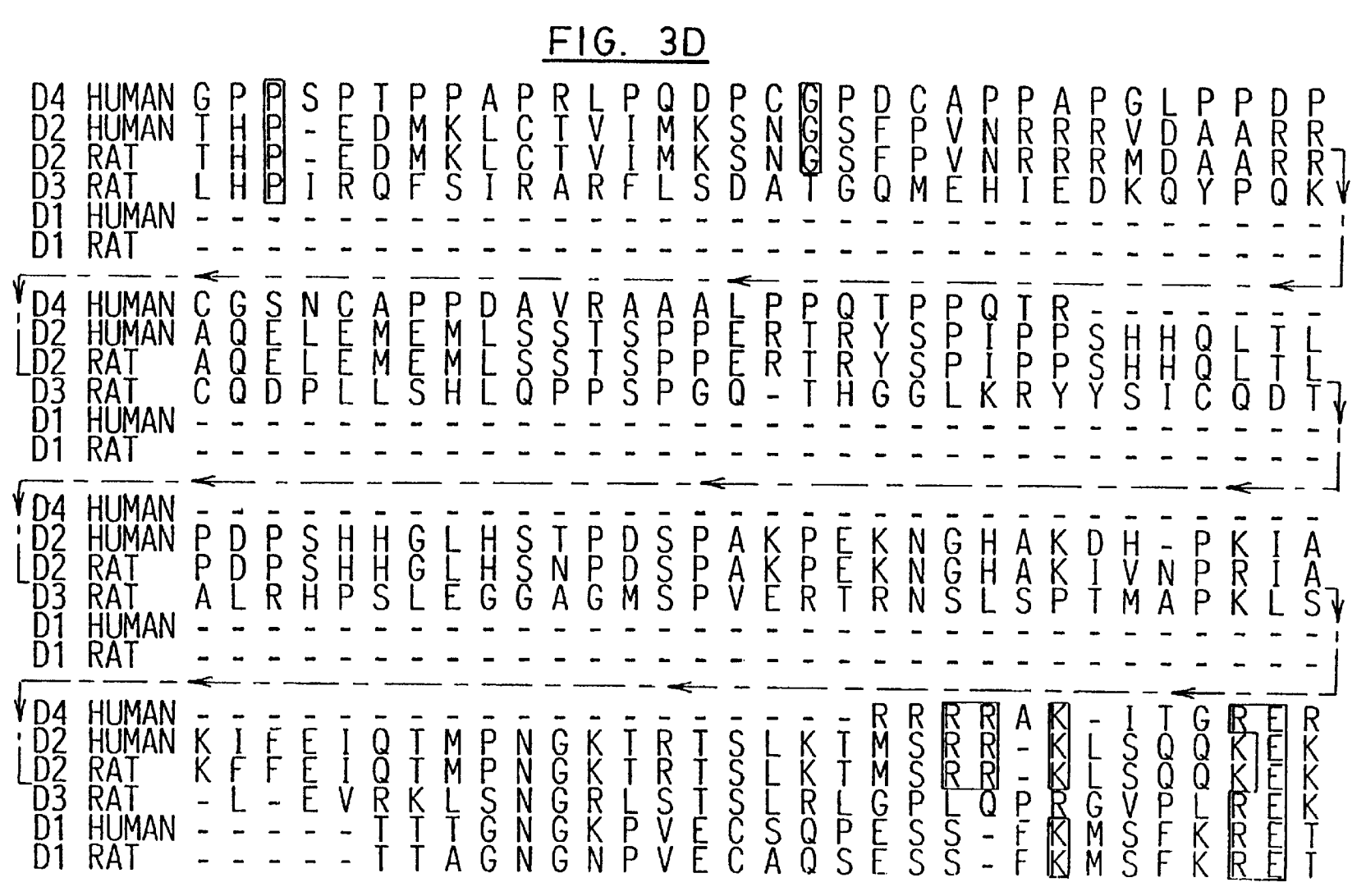

FIGS. 3A through 3F provides an amino acid sequence alignment of mammalian dopamine receptors FIG. 4 shows the binding of [$^3$H]spiperone to membranes of COS-7 cell transfected with a recombinant expression construct that expresses the human D4 receptor protein.

FIGS. 6A through 6C illustrates the structure of a genomic clone comprising the human D4 dopamine receptor gene and the nucleic acid and corresponding amino acid sequences of 2, 4 and 7 copies of a novel 48 bp tandem repeat.

SUMMARY OF THE INVENTION

Figure 1:
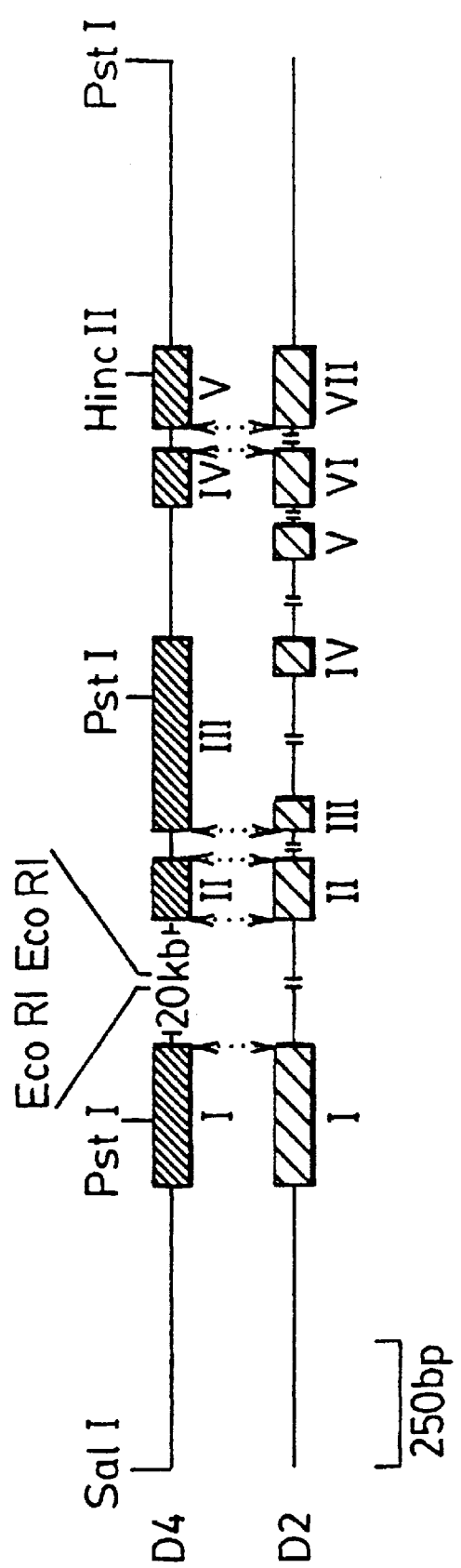
FIG. 1 illustrates the structure of a genomic clone comprising the human D4 dopamine receptor gene.
Figure 3A:
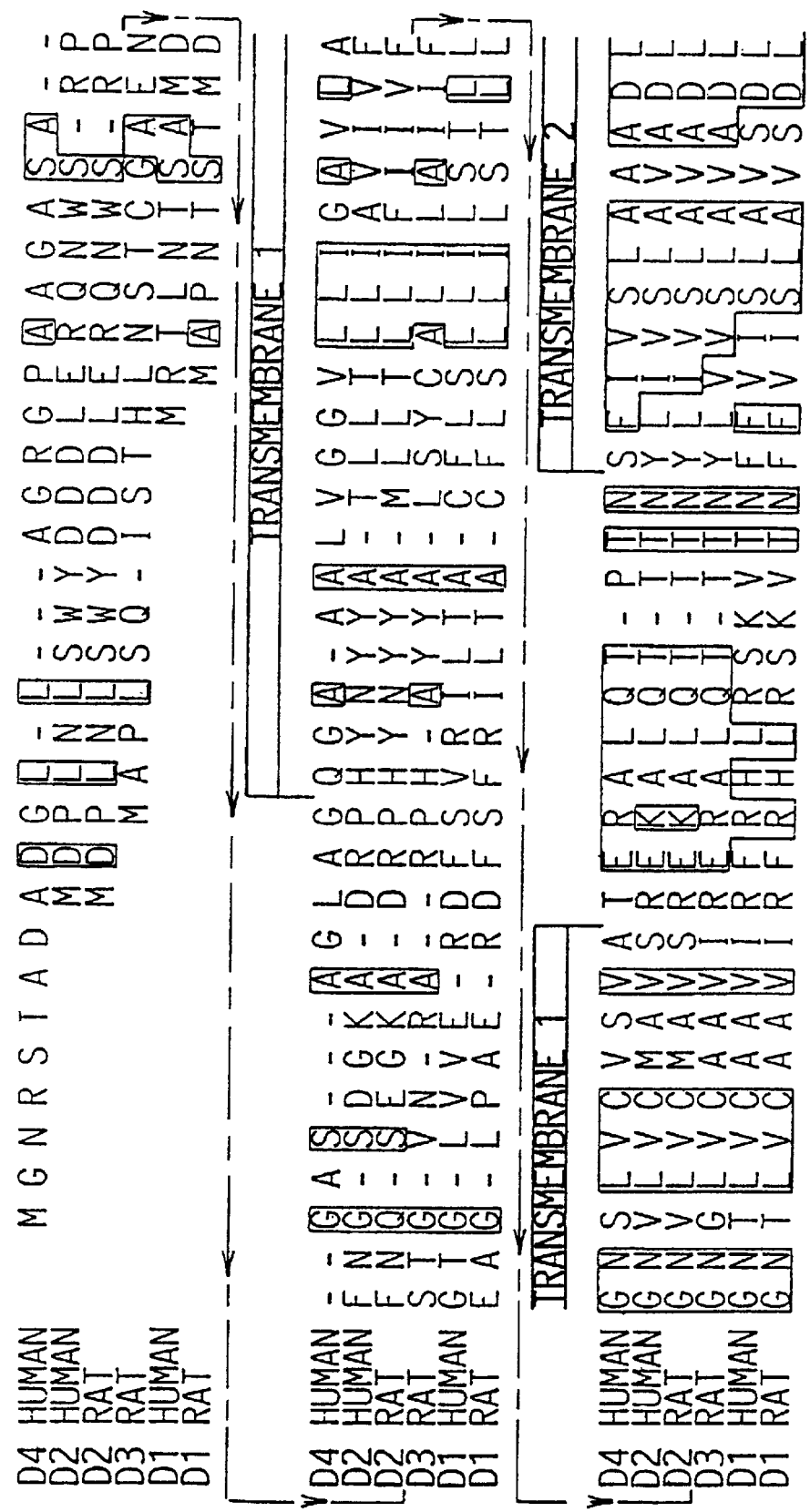
Figure 3B:
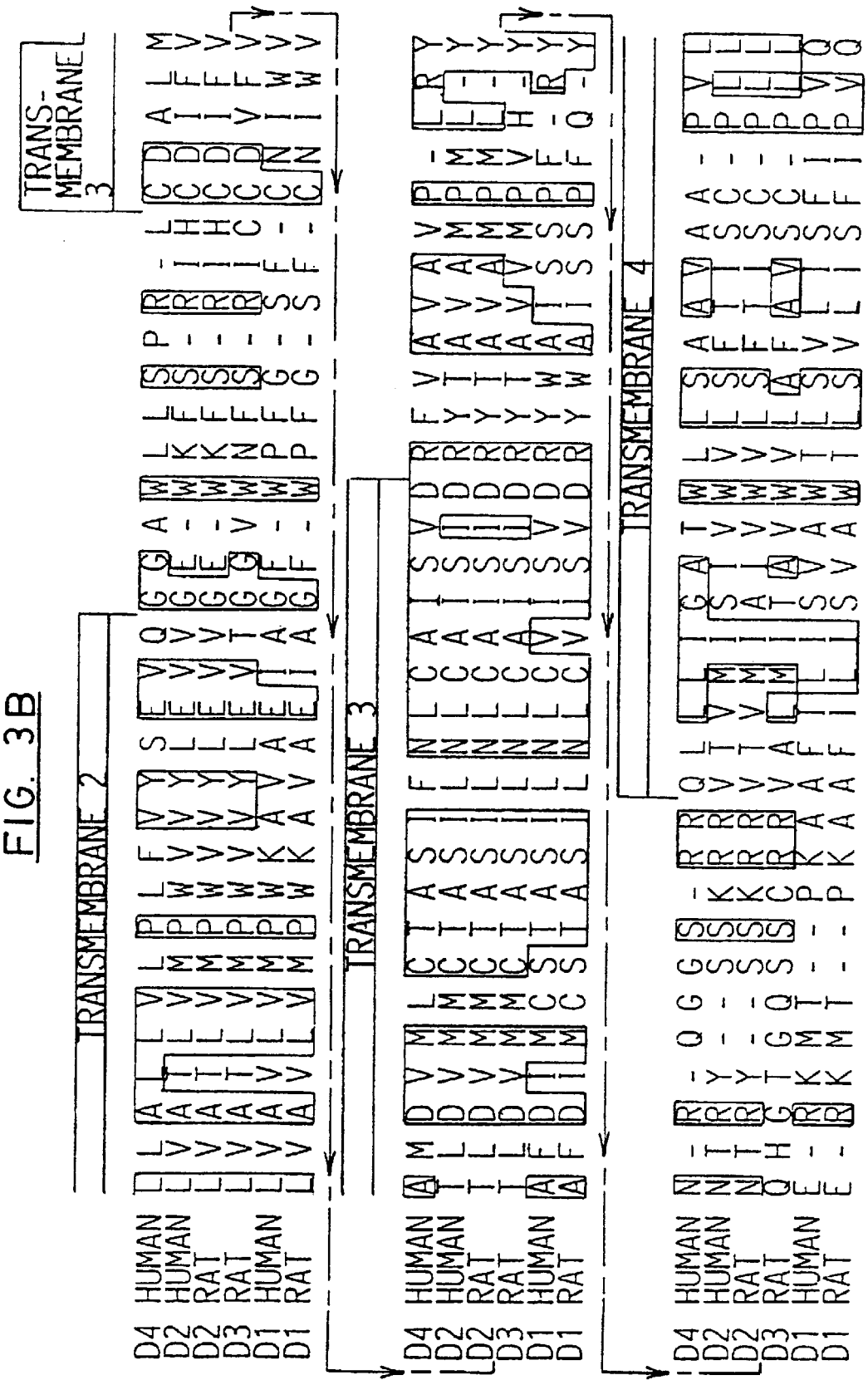
Figure 3C:
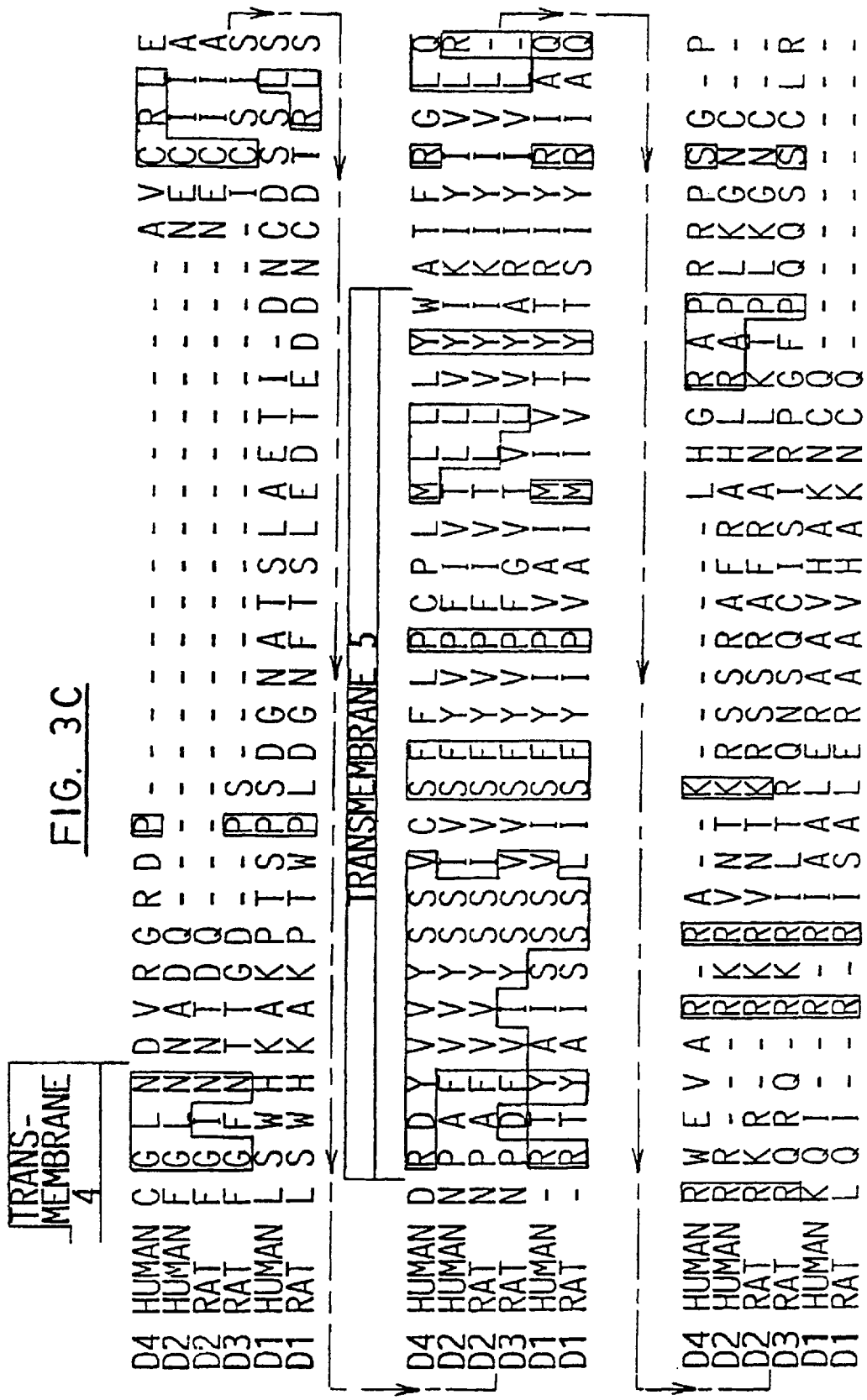
Figure 3E:
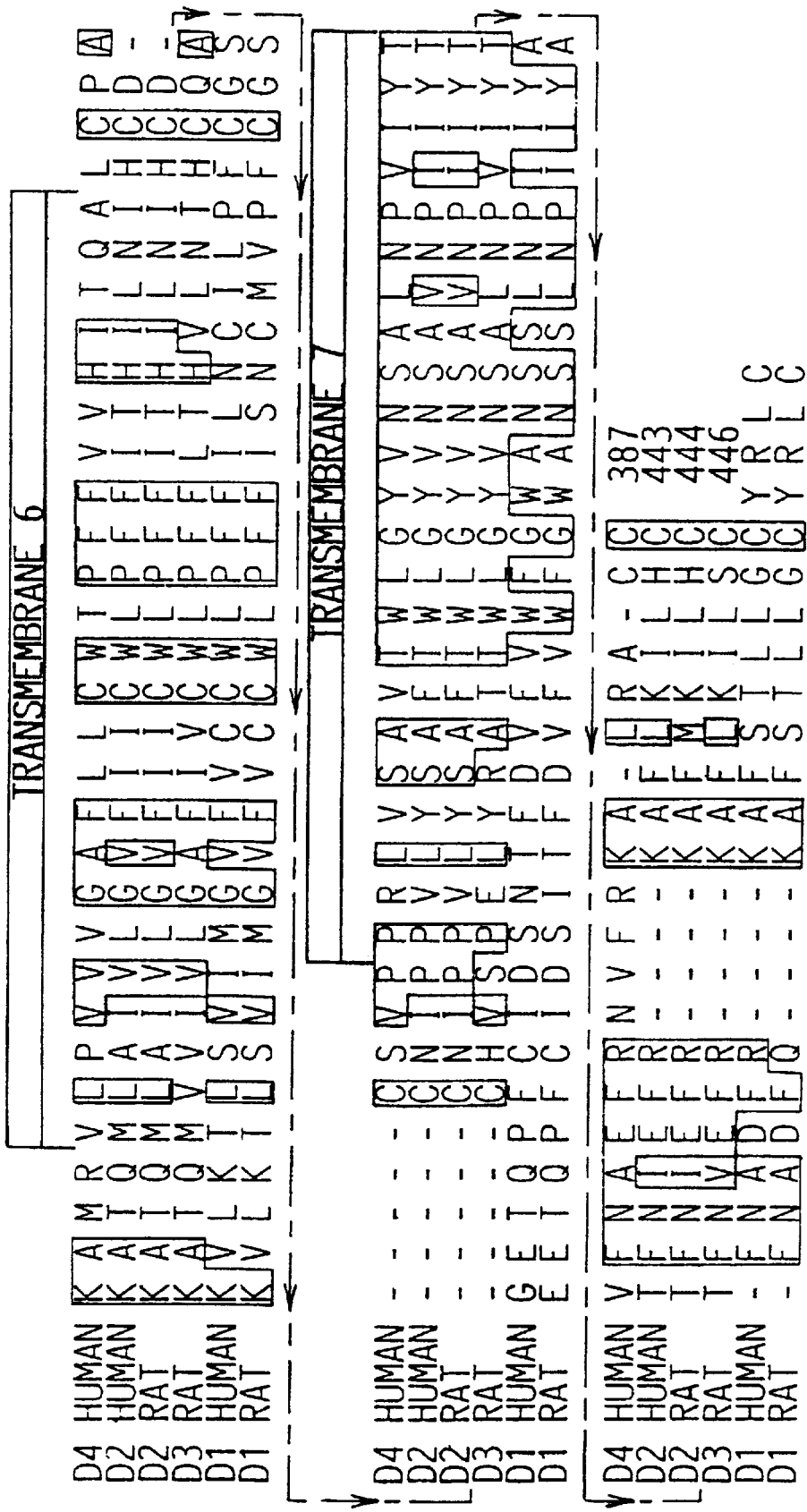

The present invention is directed toward the isolation, characterization and pharmacological use of the human D4 dopamine receptor, the gene corresponding to this receptor, a recombinant eukaryotic expression construct capable of expressing the human D4 dopamine receptor in cultures of transformed eukaryotic cells and such cultures of transformed eukaryotic cells that synthesize the human D4 dopamine receptor.

It is an object of the invention to provide a nucleotide sequence encoding a mammalian dopamine receptor. Further, it is an object of the invention to provide a nucleotide sequence that encodes a mammalian dopamine receptor with novel and distinct pharmacological properties. It is specifically an object of the invention to provide a nucleotide sequence encoding a mammalian dopamine receptor having the particular drug dissociation properties of the human dopamine receptor D4. In particular, the mammalian dopamine receptor encoded by the nucleotide sequence of the present invention has a high affinity for the drug clozapine. The human D4 dopamine receptor embodied in the present invention shows a dissociation constant (termed $K_i$) of 1–40 nanomolar (nM), preferably 1–20 nM, most preferably 11 nM clozapine, as detected by the ($^3$H) spiperone binding assay disclosed herein. The human D4 dopamine receptor embodied in the present invention displays the following pharmacological profile of inhibition of ($^3$H) spiperone binding in the ($^3$H) spiperone binding assay: spiperone>eticlopride>clozapine>(+)-butaclamol>raclopride>SCH23390. In a preferred embodiment of the invention, the nucleotide sequence encoding a dopamine receptor encodes the human dopamine receptor D4.

The present invention provides a nucleotide sequence encoding a mammalian dopamine receptor that is the human D4 receptor. In a preferred embodiment, this nucleotide sequence comprises a cDNA sequence isolated from RNA derived from the human neuroblastoma cell line SK-N-MC (SEQ ID No: 171), comprising the sequences of the D4.2 allele of the human D4 dopamine receptor gene. In another preferred embodiment, this nucleotide sequence comprises a cDNA sequence isolated from RNA derived from human pituitary gland tissue (SEQ ID No: 19). In yet another preferred embodiment, this nucleotide sequence comprises a cDNA sequence isolated from RNA derived from human substantia nigra tissue (SEQ ID No.: 19). Both of these embodiments comprise the sequences of the D4.4 allele of the human D4 dopamine receptor gene.

The invention also includes a nucleotide sequence derived from human genomic DNA (SEQ ID Nos.:1,3,4,5,7,12,14 & 15) comprising the sequences of the D4.7 allele of the human D4 dopamine receptor gene, and a nucleotide sequence derived from human genomic DNA (SEQ ID Nos.: 1,3,4,5,7,10,14 & 15) comprising the sequences of the D4.4 allele of the human D4 dopamine receptor gene. In this embodiment of the invention, the nucleotide sequence includes 5 kilobases (kb) of human genomic DNA encoding the dopamine receptor D4. This embodiment includes the sequences present in the cDNA embodiments as well as nucleotide sequences of 5' untranslated sequence, three intervening sequences that interrupt the coding sequence of the human D4 dopamine receptor gene, and 3' untranslated sequences. Also provided is a cDNA sequence derived from the genomic DNA sequence of the D4.4. allele (SEQ ID No: 19) and the D4.7 allele (SEQ ID No: 21) of the human D4 dopamine receptor gene.

The invention includes a nucleotide sequence of a human D4 receptor molecule, and includes allelic variations of this nucleotide sequence and the corresponding D4 receptor molecule, either naturally occurring or the product of in vitro chemical or genetic modification, having essentially the same nucleotide sequence as the nucleotide sequence of the human D4 receptor disclosed herein, wherein the resulting human D4 receptor molecule has substantially the same drug dissociation properties of the human D4 receptor molecule corresponding to the nucleotide sequence described herein. Specific preferred embodiments include alleles D4.2, D4.4 and D4.7 of the human D4 dopamine receptor gene, as defined herein.

The invention provides sequences of the naturally-occurring alleles of the human D4 dopamine receptor gene. Such alleles are defined as comprising from about 2 to about 8 repeats of a nucleotide sequence that is substantially homologous to the sequence (SEQ ID Nos: 8,10,12,17,19, 21):

A CCC GCG CCC CGC CTC CCC CAG GAC CCC TGC GGC CCC GAC TGT GCG CC.

Allelic variations of this nucleotide sequence and the corresponding D4 receptor molecule, either naturally occurring or the product of in vitro chemical or genetic modification, having essentially the same nucleotide sequence as the nucleotide sequence of the human D4 receptor disclosed herein, wherein the resulting human D4 receptor molecule has substantially the same drug dissociation properties of the human D4 receptor molecule corresponding to the nucleotide sequence described herein are additional preferred embodiments of the invention. Specific preferred embodiments include the allele D4.2, comprising 2 copies of the repeat tandemly repeated (SEQ ID Nos: 8 & 17); the allele D4.4, comprising 4 copies of the repeat tandemly repeated (SEQ ID Nos: 10 & 19); and the allele D4.7, comprising 7 copies of the repeat tandemly repeated (SEQ ID Nos: 12 & 21).

The invention also includes a predicted amino acid sequence for the human D4 dopamine receptor deduced from the nucleotide sequence comprising the complete coding sequence of the D4 dopamine receptor gene (SEQ ID Nos: 18, 20 & 22). Specific preferred embodiments comprise the amino acid sequence of the naturally-occurring alleles of the human D4 dopamine receptor gene. Such alleles are defined as comprising from about 2 to about 8 repeats of an amino acid sequence that is substantially homologous to the sequence (SEQ ID Nos: 9,11,13,18,20, 22):

(P/A)AP(R/G)LP(Q/R/P)(D/G)PCG(P/S)(D/N)CAP

Allelic variations of this amino acid and the corresponding D4 receptor molecule, either naturally occurring or the product of in vitro chemical or genetic modification, having essentially the same amino acid sequence as the human D4 receptor disclosed herein, wherein the human D4 receptor molecule has substantially the same drug dissociation properties of the human D4 receptor molecule corresponding to the amino acid sequence described herein are additional preferred embodiments of the invention. Specific preferred embodiments include the allele D4.2, comprising 2 copies of the repeat tandemly repeated (SEQ ID Nos: 9 & 18); the allele D4.4, comprising 4 copies of the repeat tandemly repeated (SEQ ID Nos: 11 & 20); and the allele D4.7, comprising 7 copies of the repeat tandemly repeated (SEQ ID Nos: 13 & 22).

This invention provides both nucleotide and amino acid probes derived from these sequences. The invention includes probes isolated from either cDNA or genomic DNA clones, as well as probes made synthetically with the sequence information derived therefrom. The invention specifically includes but is not limited to oligonucleotide, nick-translated, random primed, or in vitro amplified probes made using cDNA or genomic clones embodying the invention, and oligonucleotide and other synthetic probes synthesized chemically using the nucleotide sequence information of cDNA or genomic clone embodiments of the invention. The sequence information provided by the present invention is also intended to provide the basis for in vitro amplification methods for detecting D4 dopamine receptor alleles comprising the genotype of somatic and germ cells, zygotes, embryoes, and tissues in humans and other mammals for diagnostic, therapeutic and other purposes.

It is a further object of this invention to provide sequences of the human D4 dopamine receptor for use as probes to determine the pattern, amount and extent of expression of this receptor in various tissues of mammals, including humans. It is also an object of the present invention to provide probes derived from the sequences of the human D4 dopamine receptor to be used for the detection and diagnosis of genetic diseases. It is an object of this invention to provide probes derived from the sequences of the human D4 dopamine receptor to be used for the detection of novel related receptor genes.

The present invention also includes synthetic peptides made using the nucleotide sequence information comprising the cDNA or genomic clone embodiments of the invention. The invention includes either naturally occurring or synthetic peptides which may be used as antigens for the production of D4 dopamine receptor-specific antibodies, or used for competitors of the D4 receptor molecule for drug binding, or to be used for the production of inhibitors (or blockers) of the binding of dopamine or dopamine analogs of the D4 dopamine receptor molecule. As used herein, the term "inhibitor of dopamine binding" is intended to encompass biochemical agonists and/or antagonists of dopamine binding to the D4 dopamine receptor.

In addition, this invention includes recombinant DNA constructs comprising the human D4 dopamine receptor and sequences that mediate the replication and selected growth of microorganisms that carry this construct.

The present invention provides recombinant expression constructs comprising the nucleotide sequence of the human D4 dopamine receptor and sequences sufficient to direct the synthesis of the human D4 dopamine receptor protein in cultures of transformed eukaryotic cells. In preferred embodiments, the recombinant expression construct is comprised of plasmid sequences derived from the plasmid pCD-PS and D4 dopamine receptor sequences corresponding to cDNA sequences for alleles D4.2, D4.4 and D4.7, as defined herein, as well as a hybrid human D4 dopamin gene, comprised of the entirety of the genomic sequences from a particular D4 dopamine genomic clone described herein, up to a PstI site located in exon III, followed by the remainder of the coding and 3' untranslated sequences found in a particular human cDNA sequence derived from a human neuroblastoma cell line. Recombinant expression constructs of the invention also encompass embodiments comprising allelic variations of the human D4 dopamine receptor genomic DNA sequences and cDNA-derived sequences. This invention includes recombinant expression constructs comprising essentially the nucleotide sequences of genomic and CDNA clones of the human D4 dopamine receptor and allelic variations thereof in embodiments that provide for the expression of human D4 dopamine receptor protein in cultures of transformed eukaryotic cells.

It is also an object of this invention to provide cultures of transformed eukaryotic cells that have been transformed with such recombinant expression constructs and that synthesize human D4 dopamine receptor protein. In a preferred embodiment, the invention provides monkey COS cells that synthesize human D4 dopamine receptor protein.

The present invention also includes protein preparations of the human D4 dopamine receptor, and preparations of membranes containing the human D4 dopamine receptor, derived from cultures of eukaryotic cells transformed with the recombinant expression constructs of the invention. In a preferred embodiment, cell membranes containing human D4 dopamine receptor protein are isolated from culture of COS-7 cells transformed with a recombinant expression construct that directs the synthesis of human D4 dopamine receptor.

It also an object of this invention to provide the human D4 dopamine receptor for use in the in vitro screening of novel antipsychotic compounds. In a preferred embodiment, membrane preparations containing the human D4 dopamine receptor, derived from cultures of eukaryotic cells transformed with the recombinant expression constructs of the invention, are used to determine the drug dissociation properties of antipsychotic compounds in vitro. These properties are then used to characterize novel antipsychotic compounds by comparison to the binding properties of known antipsychotic compounds.

The present invention will also be useful for the detection of dopamine and dopamine analogues, known or unknown, either naturally occurring or as the embodiments of antipsychotic or other drugs.

It is an object of the present invention to provide a method for the quantitative detection of dopamine and dopamine analogues, either naturally occurring or as the embodiments of antipsychotic or other drugs. It is an additional object of the invention to provide a method to detect dopamine or dopamine analogues in blood, saliva, semen, cerebrospinal fluid, plasma, lymph, or any other bodily fluid.

DETAILED DESCRIPTION OF THE PREFERRED EMBODIMENTS

The term "D4 dopamine receptor" as used herein refers to proteins substantially homologous to, and having substantially the same biological activity as, the protein coded for by the nucleotide sequences depicted in FIGS. 2A through 2D and FIGS. 6A through 6C (i.e., proteins which display high affinity binding to clozapine) (SEQ ID Nos: 1,3,4,5,7, 8,10,12,14 & 15). This definition is intended to encompass natural allelic variations in the D4 dopamine receptor sequence, specifically including the alleles D4.2, D4.4 and D4.7, as defined herein (SEQ ID Nos.: 17,19 & 21), and all references to the D4 dopamine receptor, and nucleotide and amino acid sequences thereof are intended to encompass such allelic variations, both naturally-occurring and man-made. Cloned genes of the present invention may code for D4 dopamine receptors of any species of origin, including, mouse, rat, rabbit, cat, and human, but preferably code for receptors of mammalian, most preferably human, origin.

The production of proteins such as the D4 dopamine receptor from cloned genes by genetic engineering is well known (see, e.g., U.S. Pat. No. 4,761,371 to Bell et al. at Col. 6 line 3 to Col. 9 line 65; the disclosure of all U.S. patent references cited herein is to be incorporated herein by reference). The discussion which follows is accordingly intended as an overview of this field, and is not intended to reflect the full state of the art.

DNA which encodes the D4 dopamine receptor may be obtained, in view of the instant disclosure, by chemical synthesis, by screening reverse transcripts of mRNA from appropriate tissues, cells or cell line cultures, by screening genomic libraries from appropriate cells, or by combinations of these procedures, as illustrated below. Screening of mRNA or genomic DNA may be carried out with oligonucleotide probes generated from the D4 dopamine receptor gene sequence information-provided herein. Probes may be labeled with a detectable group such as a fluorescent group, a radioactive atom or a chemiluminescent group in accordance with known procedures and used in conventional hybridization assays, as described in greater detail in the Examples below. In the alternative, D4 dopamine receptor gene sequences may be obtained by use of the polymerase chain reaction (PCR) procedure, with the PCR oligonucleotide primers being produced from the D4-dopamine receptor gene sequence provided herein (see U.S. Pat. Nos. 4,683,195 to Mullis et al. and 4,683,202 to Mullis).

The D4 dopamine receptor may be synthesized in host cells transformed with constructs containing DNA encoding the D4 dopamine receptor. Such constructs are replicable and are used herein either to amplify DNA encoding the D4 dopamine receptor and/or to express DNA which encodes the D4 dopamine receptor. An expression construct is a replicable DNA construct in which a DNA sequence encoding the D4 receptor is operably linked to suitable control sequences capable of effecting the expression of the D4 receptor in a suitable host. The need for such control sequences will vary depending upon the host selected and the transfection method chosen. Generally, control sequences include a transcriptional promoter, an optional operator sequence to control transcription, a sequence encoding suitable mRNA ribosomal binding sites, and sequences which control the termination of transcription and translation. When used for DNA amplification such constructs do not require expression control domains. All that is needed is the ability to replicate in a host, usually conferred by an origin of replication, and a selective marker gene to facilitate recognition of transformants.

Constructs useful for practicing the present invention include plasmids, viruses (including phage), retroviruses, and integratable DNA fragments (i.e., fragments integratable into the host genome by homologous recombination). The construct may replicate and function independently of the host genome, or may, in some instances, integrate into the host genome itself. Suitable constructs will contain replicon and control sequences which are derived from species compatible with the intended expression host. Transformed host cells are cells which have been transformed, transfected or infected with the D4 receptor-containing constructs assembled using recombinant DNA techniques. Transformed host cells ordinarily express the D4 receptor, but host cells transformed for purposes of cloning or amplifying the D4 receptor DNA need not express the D4 receptor. When expressed, the D4 receptor will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in the same translational reading frame.

Cultures of cells derived from multicellular organisms are a desirable host for recombinant D4 dopamine receptor synthesis. In principal, any higher eukaryotic cell culture can be used, whether from vertebrate or invertebrate culture. However, mammalian cells are preferred, as illustrated in the Examples. Propagation of such cells in cell culture has become a routine procedure (see *Tissue Culture*, Academic Press: New York (Kruse & Patterson, eds.) 1973). Examples of useful host cell lines are VERO and HeLa cells, Chinese hamster ovary (CHO) cell lines, and WI138, BHK, COS-7, CV, and MDCK cell lines. Expression constructs for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression constructs to be used in transforming vertebrate cells are often provided by viral sources. For example, commonly used promoters are derived from polyoma, Adenovirus 2, and Simian Virus 40 (SV40; see, e.g., U.S. Pat. No. 4,599,308). The early and late promoters of SV40 are useful because both are obtained easily from the virus within a fragment which also contains the SV40 viral origin of replication (see Fiers et al., 1978, Nature 273: 113). Further, the human genomic D4 receptor promoter, control and/or signal sequences, may also be used, provided such control sequences are compatible with the host cell chosen.

An origin of replication may be provided either within the construct itself, such as may be derived from SV40 or other viral source (e.g., Polyoma, Adenovirus, VSV, or MPV), or may be provided by the host cell chromosomal replication mechanism. If the construct is integrated into the host cell chromosome, the latter may be sufficient.

D4 dopamine receptors made from cloned genes in accordance with the present invention may be used for screening compounds for D4 dopamine receptor activity, or for determining the amount of a dopaminergic drug in a solution (e.g., blood plasma or serum). For example, host cells may be transformed with a construct of the present invention, D4 dopamine receptors expressed in that host, the cells lysed, and the membranes from those cells used to screen compounds for D4 dopamine receptor binding activity. Competitive binding assays in which such procedures may be carried out are well known, as illustrated by the Examples below. By selection of host cells which do not ordinarily express a dopamine receptor, pure preparations of membranes containing D4 receptors can be obtained. Further, D4 dopamine receptor agonist and antagonists can be identified by transforming host cells with constructs of the present invention. Membranes obtained from such cells can be used in binding studies wherein the drug dissociation constants are measured. Such cells must contain D4 protein in the plasma and other cell membranes. Procedures for carrying out assays such as these are also described in greater detail in the Examples which follow.

Cloned genes and constructs of the present invention are useful to transform cells which do not ordinarily express the D4 dopamine receptor to thereafter express this receptor. Such cells are useful as intermediates for making cell membrane preparations for receptor binding assays, which are in turn useful for drug screening. Further, genes and constructs of the present invention are useful in gene therapy. For such purposes, retroviral constructs as described in U.S. Pat. No. 4,650,764 to Temin and Watanabe or U.S. Pat. No. 4,861,719 to Miller may be employed. Cloned genes of the present invention, or fragments thereof, may also be used in gene therapy carried out homologous recombination or site-directed mutagenesis (See generally Thomas & Capecchi, 1987, Cell 51: 503–512; Bertling, 1987, Bioscience Reports 7: 107112; Smithies et al., 1985, Nature 317: 230–234).

Cloned genes of the present invention, and oligonucleotides derived therefrom, are useful for screening for restriction fragment length polymorphism (RFLP) associated with genetic polymorphisms within a population. Such RFLPs may also be associated with certain genetic disorders, and the probes provided by the invention can be used for their identification and the identification of individuals susceptible to neuropsychiatric disorders such as schizophrenia and manic depression. Such RFLPs may also be useful for predicting individual responsiveness to psychotropic and antipsychotic drugs.

Oligonucleotides of the present invention are useful as diagnostic tools for probing D4 receptor gene expression in nervous tissue. For example, tissue can be probed in situ with oligonucleotide probes carrying detectable label groups by conventional autoradiography techniques, as explained in greater detail in the Examples below, to investigate native expression of this receptor or pathological conditions relating thereto. Further, chromosomes can be probed to investigate the location of the D4 dopamine receptor gene, and potential pathological conditions related thereto, as also illustrated by the Examples below.

Oligonucleotides of the present invention are also useful for in vitro amplification of D4 dopamine receptor sequences. Amplification methods include but are not intended to be limited to the polymerase chain reaction and the ligase chain reaction. Amplification of D4 dopamine receptor sequences is useful as a diagnostic tools for analyzing and quantitating D4 receptor gene expression in tissue, for example nervous tissue. Additionally, the use of oligonucleotides synthesized or isolated according to methods well known in the art that comprise D4 dopamine receptor sequences provided by the invention permit in vitro amplification methods to be used for the detection of D4 dopamine receptor alleles comprising the genotype of somatic and germ cells, zygotes, embryoes, and tissues in humans and other mammals for diagnostic, therapeutic and other purposes.

The Examples which follow are illustrative of specific embodiments of the invention, and various uses thereof. They are set forth for explanatory purposes only, and are not to be taken as limiting the invention.

EXAMPLE 1

Screening Tissue and Cell Line RNA for Dopamine Receptor Expression

RNA was prepared from different rat tissues or cell lines using the guadinium thiocyanate/CsCl procedure described in Bunzow et al., 1988, Nature 336: 783–787. Tissues tested included heart, epididymis, testis, gut, pancreas, spleen, thymus, muscle, ventricle, atria, lung, adrenal, kidney, liver, pineal gland and pituitary. Cell lines screened included SK-N-MC, SK-N-SH, COS, AKR1, Ltk, GH4C1, NG108–15, AtT20, 3T3, BSC40, C6, CV-1, Hela, IMR-32, N4TG1, NCB-20, PC-12, Rin m5f and WERI-Rb-1. 20 μg of RNA was analyzed by Northern blot hybridization with a radiolabeled BstYI-BglII DNA fragment of the rat D2 receptor, which encodes the putative transmembrane domains VI and VII. Blots were hybridized under standard conditions as described in Bunzow et al., ibid.; hybridization was performed overnight at 37° C. Blots were then washed at 55° C. in 2×standard saline-citrate (SSC) and 1% sodium dodecyl sulfate (SDS). Washed blotes were exposeed to X-ray film for two days at −70° C. using an intensifying screen. For comparison, the same blot was hybridized under high stringency conditions (the modifications of which include using 50% formamide and 42° C. for the hybridication and 0.2×SSC for the wash). Under conditions of low stringency the SK-N-MC cell line showed a positive signal in these experiments.

EXAMPLE 2

Construction of a CDNA Phage Library using Neuroblastoma RNA

Double-stranded cDNA was synthesized using standard techniques (see Sambrook et al., 1989, *Molecular Cloning: A Laboratory Manual,* 2d ed., Cold Spring Harbor Laboratory Press: New York) from poly(A)⁺ mRNA isolated from the human neuroblastoma cell line SK-N-MC as described in Example 1. The cDNA was directionally cloned into the EcoRI and XhoI restriction endonuclease sites of the phage cloning vector lambda ZAPII (Stratagene, La Jolla, Calif.). The library was transferred to colony plaque screen filters (New England Nuclear, Boston, Mass.). Approximately 500,000 independent clones were screened under low-stringency hybridization conditions as described in Example 1. Hybridization was performed for 30 hrs with $^{32}$P-labeled 1.6 kb BamHI-BglII and 300 bp BstYI-BglII fragments of a rat D2 receptor clone at a specific activity of $10^6$ dpm/μg. Filters were washed at 55° C. in 2×SSC and 1% SDS. The clone D210S was isolated and sequenced using the Sanger dideoxy chain termination method catalyzed by Sequenase (U.S. Biochemical Corporation, Cleveland, Ohio). The sequence of this clone is shown in FIGS. 2A through 2D (hatched area).

The putative coding sequence is shown in capitals, unsequenced intervening sequence noted by dots).and the deduced amino acid sequence is shown below the nucleotide sequence. Numbering of the putative coding sequence begins with the first methionine of the open reading frame. Single-letter abbreviations for amino acids and nucleotides used herein can be found in G. Zubay, Biochemistry (2d. ed.), 1988 (MacMillen Publishing: New York) p.33. Noteworthy is the presence of a duplicated 48 bp sequence in the putative third exon, corresponding to the third cytoplasmic loop region of the D4 receptor protein. The complete nucleotide sequence of this clone has been determined (see FIGS. 6A through 6C, wherein repeated sequences of this clone are designated D4.2 (SEQ ID No: 17).

EXAMPLE 3

Screening a Genomic DNA Phage Library with a Human Dopamine Receptor Probe

Clone D210S was $^{32}$P-labeled by random primed synthesis and used to screen a commercially available human genomic library cloned in the phage vector EMBL3 (Clonetech, Palo Alto, Calif.). Hybridization was performed as described in Example 2 using 50% formamide. After hybridization the filters were washed at 65° C. in 0. 1×SSC and 0.1% SDS. The clone D210G was isolated and analyzed by restriction endonuclease and Southern blot analysis. The map of this genomic clone is shown in FIG. 1, wherein the structure of the D4 receptor gene is compared with the structure of the D2 gene. Relevant restriction endonuclease sites in the D4 receptor sequence are indicated. The SalI site is part of the cloning site in EMBL3. The proposed coding regions are boxed and numbered in Roman numerals. Perfect matches of proposed intron/exon junction sites are indicated by connecting stippled bars between the receptor clones.

PstI-PstI fragments of approximately 1.3 kb and 2.6 kb, and an overlapping SalI-EcoRI fragment of approximately 2.0 kb derived from the D4 receptor gene were subcloned into the plasmid pBluescript-SK (Stratagene). The subcloned fragments were characterized by sequence analysis as described above. This sequence is shown in FIGS. 2A through 2D. The complete nucleotide sequence of this clone has been determined (see FIG. 6, wherein these repeated sequences of this clone are designated D4.7 (SEQ ID No: 21).

EXAMPLE 4

DNA Sequence Analysis of the Human D4 Dopamine Receptor

One of the cDNA clones detected by screening the SK-N-MC neuroblastoma library with a rat D2 probe at low stringency (D210S) contained a 780 bp EcoRI-XhoI insert which hybridized to the rat probe. Screening of a human genomic EMBL3 library (Clontech) under high stringency conditions with the clone D210S resulted in the isolation of the genomic clone D210G.

Southern blot and sequence analysis indicated that the clone contained a 5 kb SalI-PstI fragment which coded for the entire gene of D210S (SEQ ID No.: 21). Sequence analysis of this insert showed the presence of an open reading frame with homology to the amino acid sequence of transmembrane domains V (45%), VI (46%) and VII (78%) of the D2 receptor, shown in FIGS. 3A through 3F. The putative amino acid sequence of the human D4 receptor (SEQ ID No.: 22) is aligned with the human and rat D2, rat D3 and human and rat D1 receptor sequences. Amino acids conserved within the group of dopamine receptors are shaded. The putative transmembrane domains are overlined and labeled by Roman numerals.

There is a potential translation initiation codon (ATG) 590 bp downstream from the SalI site, followed by an open reading frame that showed amino acid sequence homology with transmembrane domain I (36%) and II (63%) of the D2 receptor. Almost immediately downstream from the transmembrane domain II sequence, homology to the D2 receptor disappears, indicating the presence of an intron in the genomic DNA. This intron spanned approximately 2 kb, after which sequence homology to the D2 receptor was re-established. Translation of the putative gene product showed homology to the transmembrane domains III (68%), IV (37%), V(46%) and VII (78%) of the D2 receptor (see FIGS. 3A through 3F).

Potential splice junction donor and acceptor sites (Mount, 1982, Nucl. Acids Res. 10: 461–472) were found in the transmembrane domains II, III and VI, as shown in FIG. 1. These splice sites were at an identical position as in the D2 and D3 receptor gene [see Grandy et al., 1989, Proc. Natl. Acad. Sci. USA 86: 9762–9766; Dal Toso et al., 1989, EMBO J. 8: 4025–4034; Sokoloff et al., 1990, Nature 347: 146–151] and FIG. 1. The coding sequence downstream from transmembrane domain IV is identical to the sequence of clone D210S but is interrupted by an intron of about 300 bp between transmembrane domains V and VI and an additional intron of 92 bp in transmembrane VI (FIG. 1, hatched area). The precise location of the splice site for the intron between transmembrane V and VI cannot be determined due to the fact that a sequence of 52 bp present in the coding sequence is repeated exactly on either side of the intron (FIGS. 2A through 2D).

The deduced amino acid sequence from the genomic and cDNA nucleotide sequences indicated that this gene codes for a protein of 387 amino acids with an apparent molecular weight of 41 kD. A hydrophobicity plot of the protein sequence suggests the existence of seven transmembrane domains. These regions correlate with the observed homologous regions in the human D2 receptor and other receptors belonging to the family of G-protein coupled receptors (Dohlman et al., 1987, Biochemistry 26: 2657–2664; Bunzow et al., 1988, Nature 336: 783–787; Sokoloff et al., 1990, Nature 347: 146-151; and FIGS. 2A through 2D). A potential N-linked glycosylation site (Hubbard & Ivatt, 1981, Ann. Rev. Biochem. 50: 555–583) is located two amino acids downstream from the initiation methionine. The amino acid residues Asp (80) and Asp (115) in the D4 receptor, which are conserved within the family catecholaminergic receptors, are postulated to act as "counterions" in catecholamine binding (Strader et al., 1988, J. Biol. Chem. 263: 10267–10271). Also conserved within the family of catecholaminergic receptors are Ser (197) and Ser (700) which have been suggested to interact with the catechol hydroxyl groups (Kozak, 1984, Nucleic Acids Res. 12: 857–872). Several consensus sites for potential phosphorylation by protein kinase C and protein kinase A are found in the third cytoplasmic loop (Sibley et al., 1987, Cell 48: 913–922; Bouvier et al., 1988, Nature D: 370–373). The Cys (187), which may serve as a substrate for palmitoylation, is conserved in most of the G-protein coupled receptors (O'Dowd et al., 1989, J. Biol. Chem 264: 7564–7569). The short carboxyl tail, which terminates similar to the D2 and D3 receptor at Cys (387) (Bunzow et al., 1988, Nature 336: 783–787; Grandy et al., 1989, Proc. Natl. Acad. Sci. USA 86: 9762–9766; Dal Toso et al., 1989, EMBO J. 8: 4025–4034; Sokoloff et al., 1990, Nature 347: 146–151), and the relatively large third cytoplasmic loop, are features observed in most receptors which interact with an isoform of the G protein.

Figures 6B, 6C:
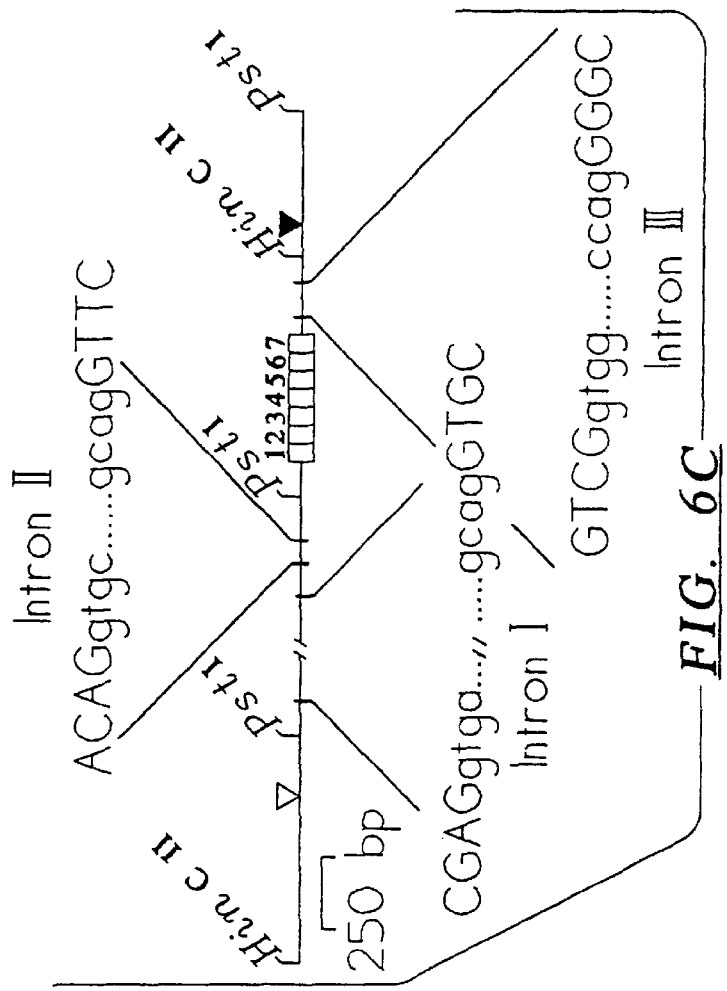

A noteworthy feature of the sequence of the third exon of the genomic D4 receptor clone is the presence of a 7-fold repeat of a GC rich, 48 bp sequence, beginning at nucleotide 447 of exon III, and encodes a proline-rich portion of the D4 dopamine receptor protein (see FIGS. 6A through 6C, wherein these sequences of this clone are designated D4.7 (SEQ ID No.:21). This region of the protein corresponds to the putative third cytoplasmic loop of the receptor protein molecule (SEQ ID No.: 22). This sequence corresponds to the 2-fold repeat of a homologous sequence found in the SK-N-MC neuroblastoma cDNA sequence described in Example 2, suggesting that the D4 receptor gene may be polymorphic. This sequence is uniquely found in the D4 receptor and is not homologous to any other known dopamine receptor protein. Interestingly, this region of the human D4 receptor is not found in the rat homologue of the D4 receptor, making this variation specific to humans.

From these results we have concluded that the sequences we have isolated encode a polymorphic member of the dopamine receptor family.

EXAMPLE 5

Construction of an Mammalian DNA Expression Construct using Dogamine Receptor cDNA The ApaI-PstI gene fragment (FIG. 1, the PstI site found in exon III after transmembrane domain V) was ligated to the corresponding PstI-EcoRI cDNA fragment isolated from the SK-N-MC cDNA. This construct was then cloned into the vector pCD-PS (Bonner et al., 1988, Neuron 1: 403–410). This vector allows for the expression of the human D4 receptor gene fom the SV40 promoter. Large quantities of the pCD-PS-D4 construct plasmid were prepared using standard techniques (see, Sambrook et al., ibid.). This plasmid was transfected into COS-7 cells by the calcium phosphate precipitation technique (Gorman et al., 1983, Science 221: 551–553). Two days later membranes cells were harvested and analyzed as described in Example 6

EXAMPLE 6

Analysis of Dopamine and Dopamine-Antagonist Binding of D4 Dopamine Receptor Cells were harvested and homogenized using a teflon pestle in 50 mM Tris-HCl (pH 7.4 at 4° C.) buffer containing 5 mM EDTA, 1.5 mM $CaCl_2$, 5 mM $MgCl_2$, 5 mM KCl and 120 mM NaCl. Homogenates were centrifuged for 15 minutes at 39,000 g, and the resulting pellets resuspended in buffer at a concentration of 150–250 μg/ml. For saturation experiments, 0.25 ml aliquots of each tissue homogenate was incubated in duplicate with increasing concentrations of $^3H$ spiperone (70.3 Ci/mmol; 10–3000 pM final concentration) for 120 min at 22° C. in a total volume of 1 ml. The results of these experiments are shown in FIG. 4. The results shown are representative of two independent experiments each conducted in duplicate (the inset show a Scatcherd plot same data). Estimated $B_{max}$ (approximately 260 fmol protein) and $K_i$ (70 pM) values were obtained by LIGAND computer program.

Figure 5:
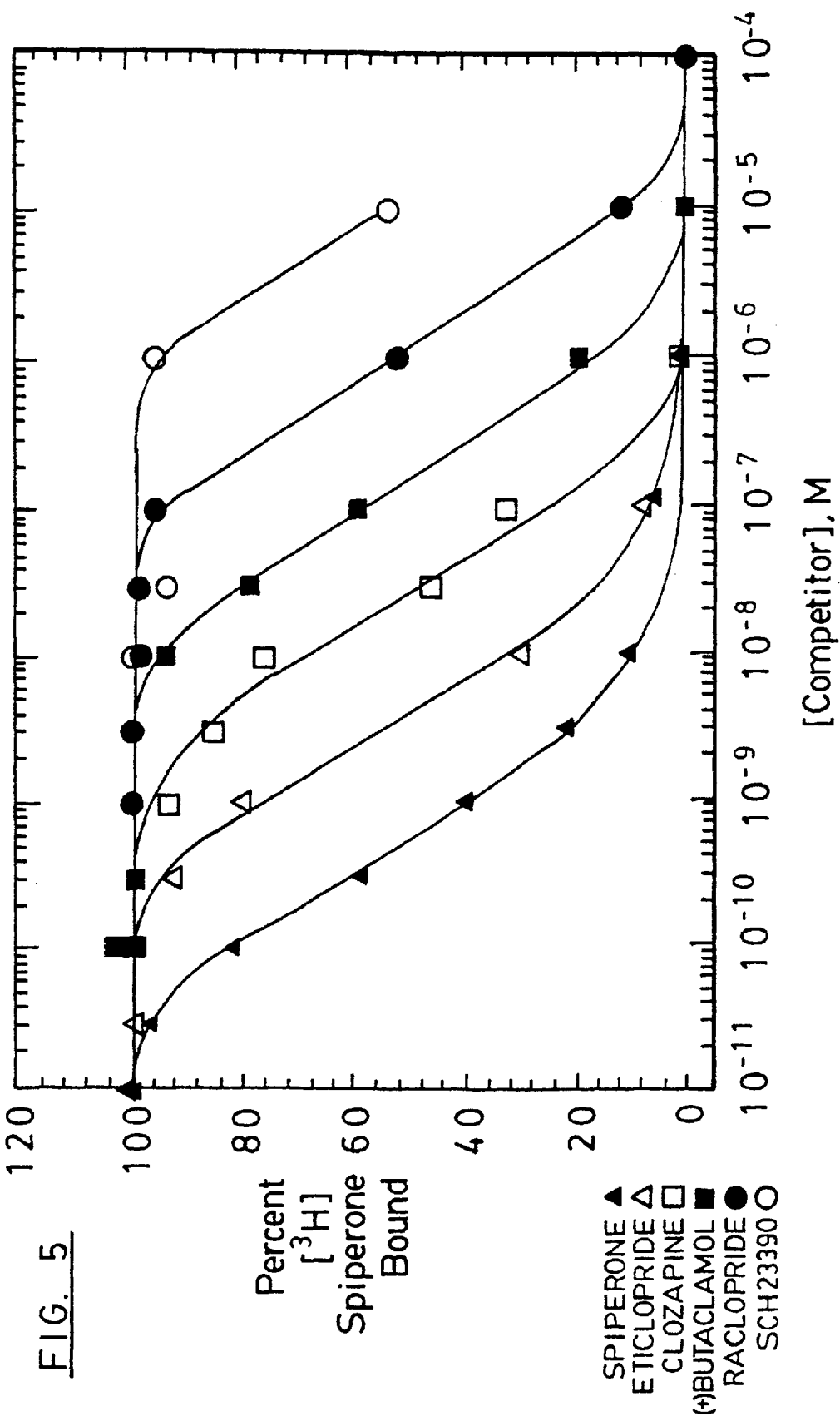
FIG. 5 demonstrates the pharmacological specificity of [$^3$H]spiperone binding to COS-7 cells transfected with a human D4 receptor expression construct.

Representative curves are shown in FIG. 5 for the concentration dependent inhibition of ($^3H$ spiperone binding by various dopaminergic agonist and antagonists. Estimated $K_i$ values are listed in Table I along with the $K_i$ values obtained on the human D2 receptor expressed in GH(4)ZR(7) cells. For competition binding experiments, assays were initiated by the addition of 0.25 ml of membrane preparation and incubated in duplicate with the concentrations of competing ligands indicated in FIG. 5 ($10^{-14}$ to $10^{-3}$ M) and [$^3H$] spiperone (150–300 pM) for 120 min at 22° C. Assays were terminated by rapid filtration through a Titertek cell harvester and filters subsequently monitored to quantitate radioactive tritium. For all experiments, specific ($^3H$) spiperone binding was defined as that binding inhibited by 10 μM (+)sulpiride. Both saturation and competition binding data were analyzed by the non-linear least square curve-fitting program LIGAND run on a Digital Micro-PDP-11. The human D4 dopamine receptor displays the following pharmacological profile of inhibition of ($^3H$) spiperone binding in this assay: spiperone>eticlopride>clozapine>(+)-butaclamol>raclopride>SCH23390.

TABLE I

Dopamine Receptor Drugs Dissociation Constants

| Dopamine Antagonists | $D_2K_i$ | | $D_4K_i$ | $D_2K_i/D_4K_i$ |
|---|---|---|---|---|
| Butaclamol-(+) | 0.9 | H | 36 | 0.03 |
| Chlorpromazine | 2.8 | R | 23 | 0.12 |
| Chlorpromazine | 1.5 | H | 23 | 0.07 |
| Clozapine | ~130 | T | 11 | 11.8 |
| Clozapine | 56 | R | 11 | 5.1 |
| Clozapine | 158 | H | 11 | 15.3 |
| Efrclopnde | 0.09 | T | 0.52 | 0.17 |
| Fluphenazine | 0.5 | T | 42 | 0.01 |
| Haloperidol | 0.5 | R | 4.5 | 0.11 |
| Haloperidol | 0.8 | R | 4.5 | 0.18 |
| Haloperidol | 1 | H | 4.5 | 0.22 |
| Ketanserin | 192 | T | 147 | 1.31 |
| Octoclothepin-S | 1.5 | T | 0.8 | 1.58 |
| Octoclothepin-R | 13.5 | T | 1.9 | 7.11 |
| Pimozide | 2.4 | R | 25 | 0.1 |
| Raclopride | 1.8 | R | 253 | 0.01 |
| Raclopride | 1.6 | H | 253 | 0.01 |
| *Raclopride | 3.2 | H | 253 | 0.01 |
| Remoxipride | ~300 | T | 2730 | 0.11 |
| SCH23390 | 913 | H | 1960 | 0.47 |
| Spiperone | 0.069 | R | 0.06 | 1.15 |
| Spiperone | 0.053 | H | 0.06 | 0.88 |
| *Spiperone | 0.05 | H | 0.06 | 0.83 |
| *Spiperone | 0.09 | H | 0.06 | 1.5 |
| Sulpiride-S | 9.2 | R | 63 | 0.02 |
| Sulpiride-S | 4.8 | R | 63 | 0.08 |
| Sulpiride-S | 46 | H | 63 | 0.73 |
| Sulpiride-S | 15.9 | H | 63 | 0.25 |
| Thioproperazine | 0.21 | R | 53 | 0.004 |
| Thioridazine | 3.3 | H | 12 | 0.28 |
| Trifluoperazine | 1.2 | T | 2.2 | 0.55 |
| YM-09151-2 | 0.06 | T | 0.11 | 0.55 |
| *YM-09151-2 | 0.09 | H | 0.11 | 0.82 |
| Dopamine Agonists | | | | |
| ADTN-(±) | 1.7 | T | 33.7 | |
| Apomorphine | ~2 | T | 3.3 | |
| Apomorphine | 24 | R | | |
| Bromocriptine | 5.3 | R | 128 | |
| Bromocriptine | 14 | H | | |
| Dopamine | 7.5 | T | 18.6 | |
| Dopamine | 2.8 | R | | |
| Dopamine | 474 | R | | |
| Dopamine + Guanine nucleotide | 1705 | R | 49 | |
| Ergocriptine-S | 0.4 | T | 55 | |
| Fencidopam | 2.8 | T | 420 | |
| N-0437 | 0.7 | T | 93 | |
| (−) Noradrenaline | ~6,000 | T | ~6,000 | |
| NPA | 0.4 | T | 5.5 | |
| PHNO-(+) | 1.2 | T | 42 | |
| Quinpirole(±) | 576 | R | | |
| Quinpirole(−) | 4.8 | T | 17 | |
| Serotonin | ~10,000 | T | ~8,000 | |
| SKF-38393 | 157 | T | 1600 | |
| SKF-38393 | 9560 | R | | | where R = rat D2 (long); H = human D2 (long) and T = $K_i$ in pig anterior pituitary homogenates-

EXAMPLE 7

Polymorphic Allelic Variants of the D4 Dopamine Receptor Isolated from Human Tissue cDNA Libraries Human cDNA libraries were screened for expression of polymorphic variants of the human D4 receptor gene. A human substantia nigra cDNA library construced in lambda gt11 (Clontech) and a pituitary cDNA library constructed in lambda gt10 as described in Example 2 were screened for clones encoding the D4 receptor. Approximately 0.5–1×10⁶ plaque-forming units (p.f.u.) were transferred in duplicate to nylon filters (DuPont/NEN) and probed with a $^{32}$P-labeled 700 bp EcoRI-XhoI fragment encoding the cDNA isolated from the neuroepithelioma SK-N-MC under conditions as described in Example 2 above.

Screening of cDNA libraries from human pituitary and substantia nigra resulted in the isolation of variant cDNA clones of the D4 receptor. The pituitary lambda gt10 clone contained a 1.4-kb EcoRI insert, coding for intron 1 and the down-stream sequences of the D4 receptor. This pituitary D4 receptor clone also contained the second intron, but the last intron was spliced out. The isolated substantia nigra lambda gt 11 clone contained a 600-bp EcoRI insert, coding for the D4 receptor, starting in the 5' site of the putative third cytoplasmic loop. Both these clones contained a four-fold repeat (see FIGS. 6A through 6C, wherein these sequences of these clones are designated D4.4 (SEQ ID No.: 19) of the 48-bp sequence previously found as a 7-fold repeat in the D4 genomic clone D210G (Example 4) and a 2-fold repeat in the neuroblastoma SK-N- MC cDNA clone (Example 2) within the putative third cytoplasmic loop of the D4 receptor protein (compare, SEQ ID Nos.: 18, 20 & 22). A comparison of the nucleic acid sequences revealed that, due to the absence of conventional splice junction sites in the seven-fold repeat sequence of the genomic clone, a novel splicing mechanism would be required to account for the existence of the different cDNA clones.

Two different human genomic libraries from different human individuals (Clontech) were screened to detect allelic polymorphism in the human D4 receptor gene. Screening of genomic libraries resulted in the isolation of a genomic clone with a 4-fold repeat of the 48 bp sequence previously detected in pituitary and substantia nigra cDNA. This result indicated that the polymorphic cDNA molecules resulted from genetic polymorphic variation in the corresponding genomic DNA, due to the existence of polymorphic alleles in the human population for the D4 receptor.

EXAMPLE 8

Additional D4 Receptor Gene Allelic Variants Found by RFLP Analysis of Human Genomic DNA The three different D4 receptor sequences predict a restriction fragment length polymorphism for a HincII-PstI fragment of the D4 gene (FIGS. 6A through 6C). Southern blot analysis of human genomic DNA was performed as described (see Sambrook et al., ibid. and Example 3). A RFLP was observed in humans and the different allelic fragments were sized.

Figure 7:
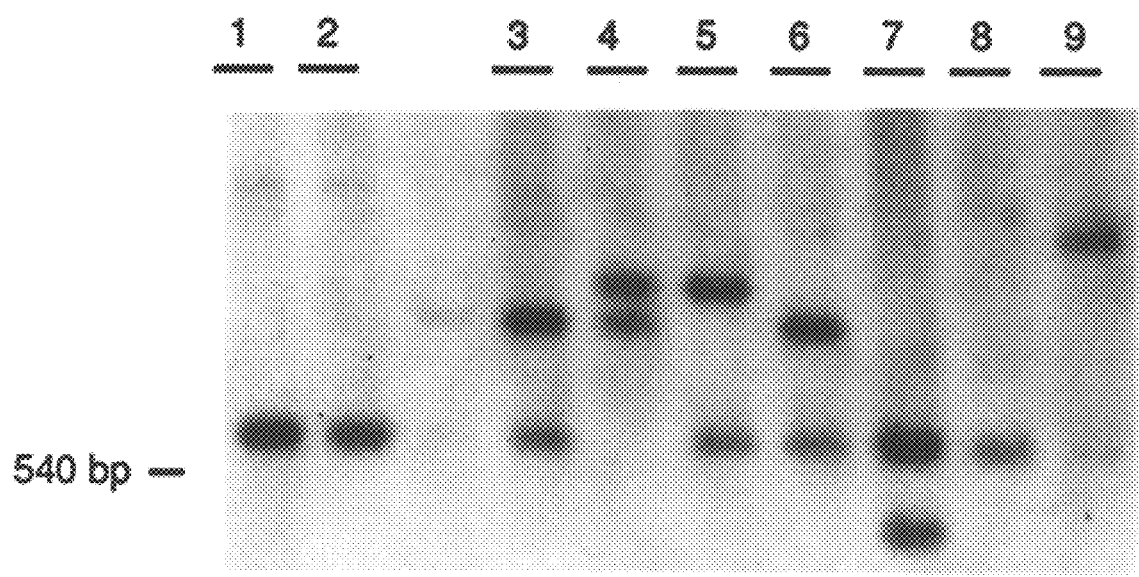
FIG. 7 illustrates restriction fragment length polymorphic variants of the human D4 receptor gene in 9 individuals.

Briefly, high molecular weight genomic DNA was isolated from human blood samples using proteinase K and phenol/chloroform extractions. Genomic DNA (5 µg) was digested with the restriction endonucleases HincII and PstI and size separated by agarose (1%) gel electrophoresis. DNA was transferred to nylon membranes (Zeta-probe, Biorad) according to standard techniques (Sambrook et al., ibid.). Southern blots were probed with a $^{32}$P-labeled 600 bp EcoRI-HincII fragment, coding for the D4 cDNA isolated from the neuroepithelioma SK-N-MC, and washed at high stringency (65° C., 0.1×SSC, 0.1% SDS, 40 min). The blot was exposed to X-ray film for three days. Results of these experiments are shown in FIG. 7.

The position of a 540-bp size marker is indicated on the left. D4-hybridizing polymorphic bands can be seen at approximately 520 bp, 620 bp, 710 bp, 760 bp and 800 bp.

[It will be recognized to those with skill in this art that the sizes given herein for the alleles of the human D4 dopamine receptor gene are limited in their precision to the resolving power of the agarose gels used in the analyses. The sizes are approximate as given herein, and more exact sizes can be calculated from the sequences of the different alleles found in SEQ ID Nos: 17, 19 & 21.] The 520 bp, 620 bp and 760 bp fragments correlate closely with the sizes of the HincII-PstII fragments of the cloned D4 receptor variants with the two-, four-and seven-fold repeat sequences respectively. The presence of 710 bp and 800 bp fragments suggests that variants with six-fold and eight-fold repeat sequences also exist. Additional population screening experiments have resulted in the detection of alleles corresponding to three-fold and five-fold repeats. A total of 7 alleles of the D4 receptor gene have accordingly been found in the human population.

EXAMPLE 9

Expression of Allelic Variants of the D4 Receptor

Mammalian DNA expression constructs were made as described in Example 5 for expression of the allelic variants of the D4 receptor. Various cDNA constructs were cloned into the expression vector PCD-PS (see Example 5) which contains the SV40 origin of replication and drives expression of the cloned inserts from the SV40 late promotor. A 1.7-kb KpnI-XbaI fragment comprising a cDNA for the D4 receptor gene containing the 7-fold repeat was cloned into the pCD-PS vector of Example 5 and called hereafter pCD-D4.7. Full-length cDNA clones for the D4.2 and D4.4 forms of the receptor were made by in vitro recombination between partial cDNA clones of these forms with the full-length cDNA clone of the D4.7 receptor variant. The clone pCD-D4.4 was created by substituting the 920-bp PstI-EcoRI 3' fragment of pCD-D4.7 with the 730-bp PstI-EcoRI fragment of the D4 cDNA isolated from human pituitary. In a similar fashion the clone pCD-D4.2 was constructed by exchange of this 3' PstI-EcoRI fragment of pCD-D4.7 with a 630-bp PstI-EcoRI fragment of the D4.2 cDNA clone isolated from the neuroepithelioma SK-N-MC.

Figure 8:
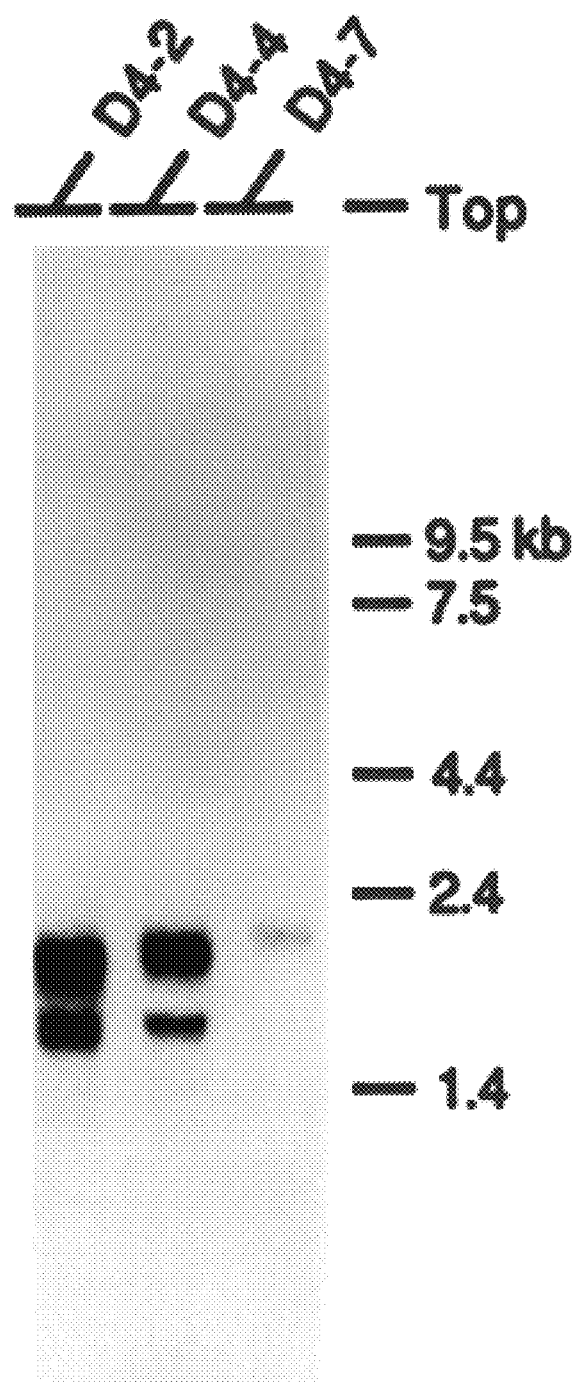
FIG. 8 demonstrates the transcriptional integrity of each of three cloned variant human D4 receptor gene expression constructs expressed in transfected COS-7 cells.

Transient expression in COS-7 cells was achieved as follows. Cells harvested and washed in phosphate buffered saline (PBS). 5×10⁷ cells were resuspended in 1 ml PBS with 100 µg/ml plasmid DNA (purified by caesium chloride gradient centrifugation) and incubated for 10 min on ice. Next, 400 µl aliquots of the cell suspension were subjected to an electric field of 0.65 kV/cm, 4.1 ms pulse duration using a BTX 600 Electro Cell Manipulator (Biotechnologies & Experimental Research, Inc., San Diego, Calif.). After the electric pulse, the cells were incubated for another 10 min on ice and then seeded in Modified Eagle's Medium supplemented with 10% fetal calf serum. The next day the medium was renewed. Three days after electroporation the cells were harvested and stored at −80° C. until use in receptor binding studies as described herein Expression of each of the cloned variant D4 receptor constructs was demonstrated by Northern blot analysis as described in Example 1. Blots were hybridized with the 700 bp EcoRI-XhoI fragment of the D4 cDNA isolated from the neuroepithelioma SK-N-MC (Example 2). The results of these experiments are shown in FIG. 8. Transient expression of the three forms in COS-7 cells as characterized in these experiments demonstrated the expected size and size differences between the three forms, indicating that none of the expressed D4 receptor RNAs are further processed or produced from one another by RNA splicing events.

Furthermore, the two bands observed for the D4.2 and D4.4 clones represent the consequence of the use of either the endogenous D4 receptor polyadenylation signal or the SV40 (vector-derived) polyadenylation signal). These observations indicate that in the transient expression system the expression of the three different clones would result in the formation of three structurally different receptors.

EXAMPLE 10

Figure 9A:
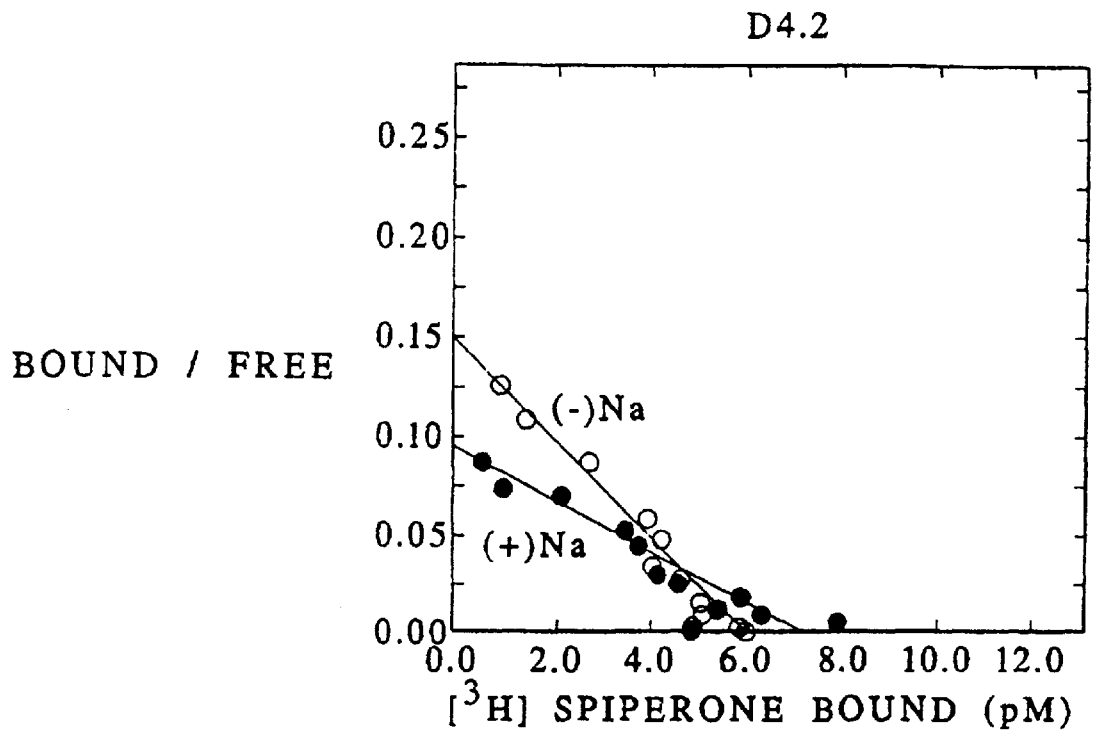
FIGS. 9A through 9C illustrate Scatchard analysis of each of three cloned variant human D4 dopamine receptor gene expression constructs expressed in transfected COS-7 cells.
Figure 9B:
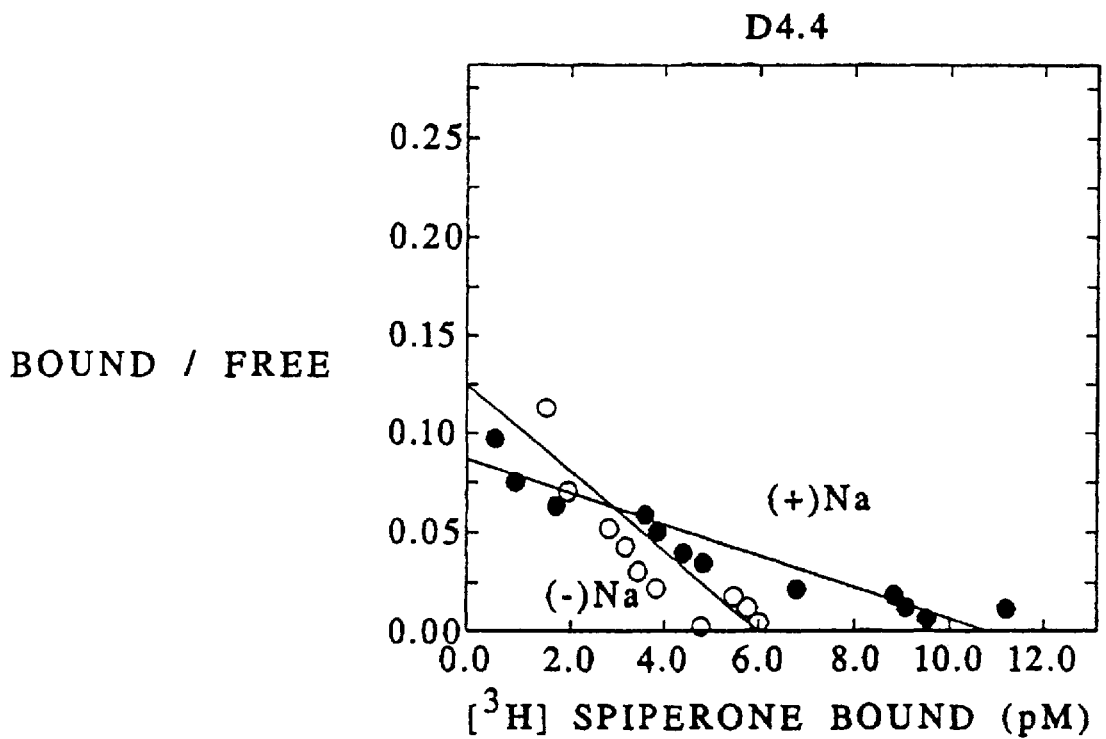
Figure 9C:
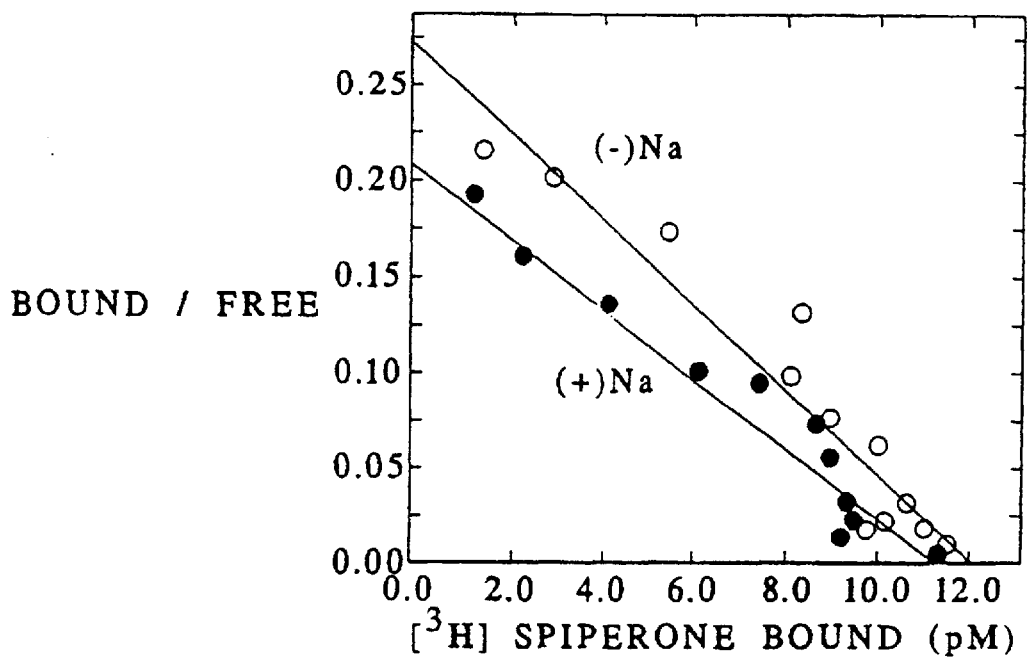
Figure 9D:
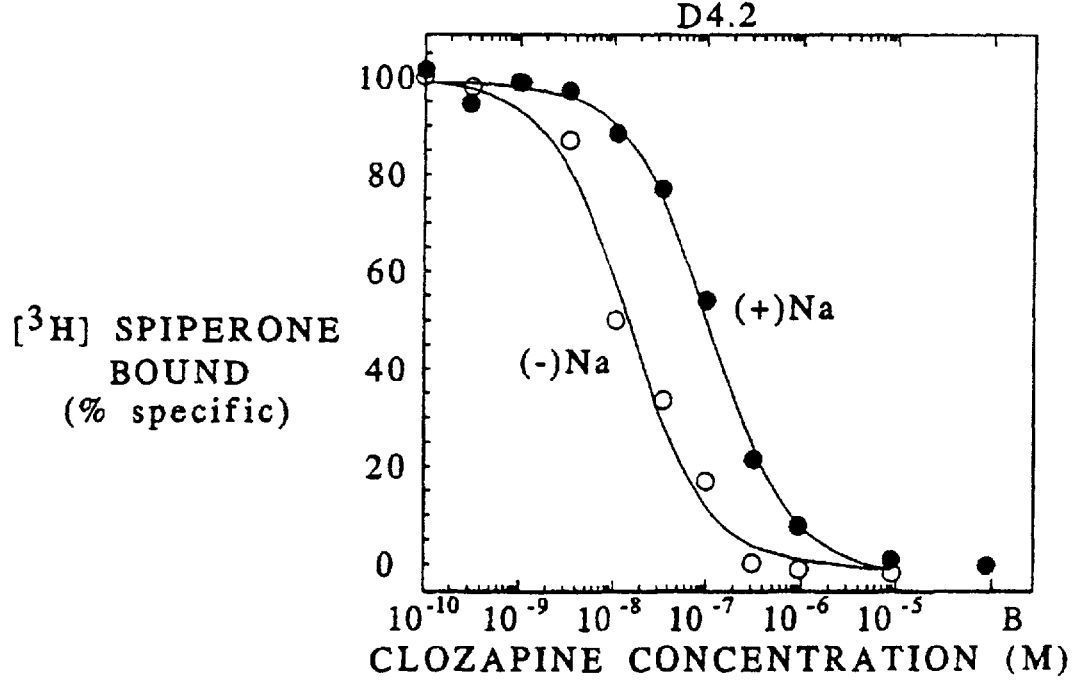
FIGS. 9D through 9F illustrate ($^3$H)-spiperone competition binding experiments of each of three cloned variant human D4 dopamine receptor gene expression constructs expressed in transfected COS-7 cells.
Figure 9E:
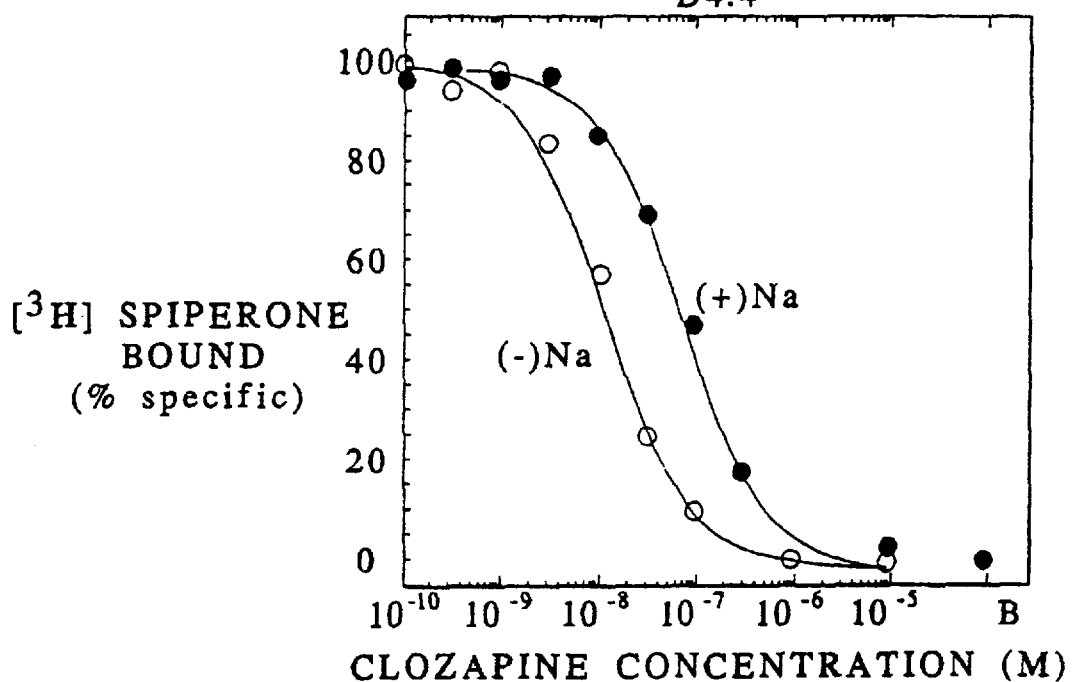
Figure 9F:
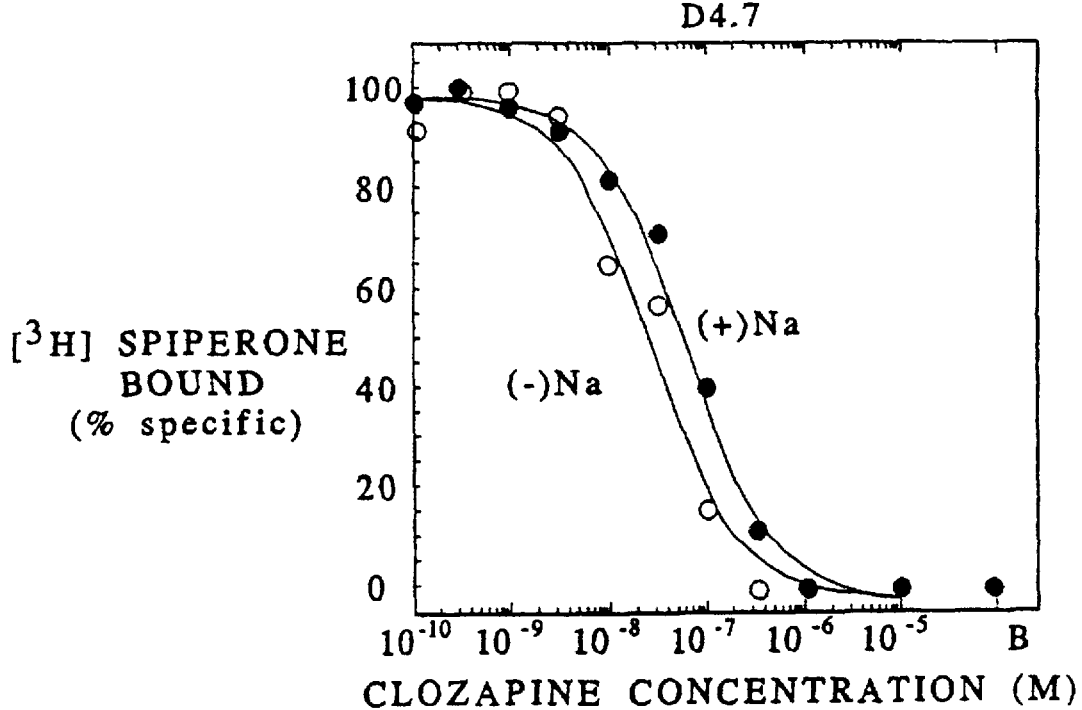

Analysis of Dopamine and Dopamine-Antagonist Binding of Variant D4 Dopamine Receptors Pharmacological analysis of dopamine agonist and antagonist binding was performed as described in Example 6. The results of these experiments are shown in FIGS. 9A through 9F. FIGS. 9A through 9C illustrate Scatchard analysis of the saturation isotherms for [$^3$H]spiperone binding to membranes prepared from COS-7 cells transiently transfected with pCD-D4.2 (D4.2), pCD-D4.4 (D4.4) and pCD-D4.7 (D4.7). FIGS 9D through 9F show clozapine competition of [$^3$H]spiperone binding for the three allelic forms of the D4 receptor in the presence (+Na$^+$) and absence (-Na$^+$) of sodium chloride.

Pharmacological analysis demonstrated that all three variants displayed saturable ($^3$H) spiperone binding (300–1000 fmol mg$^{-1}$) with similar dissociation constants in the absence of sodium chloride ($K_d$=40–50 pM; FIG. 4A). However, in the presence of 120 mM sodium chloride, the dissociation constants increased approximately two- to three-fold for D4.2 and D4.4 but not for D4.7.

Clozapine competition of ($^3$H) spiperone binding revealed that D4.2 and D4.4 had lower dissociation constants for clozapine in the absence of sodium chloride ($K_i$32 3 nM without sodiumn chloride; $K_i$=23 nM with sodium chloride). D4.7 had a dissociation constant of approximately 15 nM for clozapine which did not exhibit sodium chloride sensitivity ($K_i$=12 nM without sodium chloride; $K_i$=18 nM with sodium chloride; shown in FIG. 4B). This sodium chloride-mediated effect for clozapine on the D4 variants was not modulated by guanine nucleotides.

Agonists and antagonists (dopamine, bromocriptine, raclopride and clozapine) inhibited ($^3$H) spiperone binding (in the presence of sodium chloride) to these different D4 receptor variants in a concentration-dependent manner with similar dissociations constants. Furthermore, all three variants exhibited a guanine nucleotide-sensitive high-affinity form of the receptor upon competition with dopamine, suggesting that all these variants can functionally couple to G-proteins. Thus, we have defined a novel, polymorphic dopamine receptor which we term D4.

It should be understood that the foregoing disclosure emphasizes certain specific embodiments of the invention and that all modifications or alternatives equivalent thereto are within the spirit and scope of the invention as set forth in the appended claims.

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 388 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: 5'UTR
      (B) LOCATION: 1..103

(ix) FEATURE:
      (A) NAME/KEY: exon
      (B) LOCATION: 104..388

(ix) FEATURE:
      (A) NAME/KEY: CDS
      (B) LOCATION: 104..388

(x) PUBLICATION INFORMATION:
      (A) AUTHORS: Van Tol, Hubert H.M.
          Wu, Caren M.
          Guan, Hong-Chang
          Ohara, Koichi
          Bunzow, James R.
          Civelli, Olivier
          Kennedy, James
          Seeman, Phillip
          Niznik, Hyman B.
          Jovanovic, Vera
      (B) TITLE: Multiple dopamine D4 receptor variants in the human population
         (C) JOURNAL: Nature
         (D) VOLUME: 358
         (F) PAGES: 149-152
         (G) DATE: 9 JULY-1992

(x) PUBLICATION INFORMATION:
         (A) AUTHORS: Van Tol, Hubert H.M.
                     Bunzow, James R.
                     Guan, Hong-Chang
                     Sunahara, Roger K.
                     Seeman, Phillip
                     Niznik, Hyman B.
                     Civelli, Olivier
         (B) TITLE: Cloning of the gene for a human dopamine D4
                    receptor with high affinity for the antipsychotic
                    clozapine
         (C) JOURNAL: Nature
         (D) VOLUME: 350
         (F) PAGES: 610-614
         (G) DATE: 18 April-1991
         (K) RELEVANT RESIDUES IN SEQ ID NO:1: FROM 1 TO 388

(xi) SEQUENCE DESCRIPTION: SEQ ID NO:1:

```
CGGGGGCGGG ACCAGGGTCC GGCCGGGGCG TGCCCCCGGG GAGGGACTCC CCGGCTTGCC       60

CCCCGGCGTT GTCCGCGGTG CTCAGCGCCC GCCCGGGCGC GCC ATG GGG AAC CGC       115
                                                Met Gly Asn Arg
                                                  1

AGC ACC GCG GAC GCG GAC GGG CTG CTG GCT GGG CGC GGG CGG GCC GCG       163
Ser Thr Ala Asp Ala Asp Gly Leu Leu Ala Gly Arg Gly Arg Ala Ala
  5              10                  15                  20

GGG GCA TCT GCG GGG GCA TCT GCG GGG CTG GCT GGG CAG GGC GCG GCG       211
Gly Ala Ser Ala Gly Ala Ser Ala Gly Leu Ala Gly Gln Gly Ala Ala
             25                  30                  35

GCG CTG GTG GGG GGC GTG CTC CTC ATC GGC GCG GTG CTC GCG GGG AAC       259
Ala Leu Val Gly Gly Val Leu Leu Ile Gly Ala Val Leu Ala Gly Asn
         40                  45                  50

TCG CTC GTG TGC GTG AGC GTG GCC ACC GAG CGC GCC CTG CAG ACG CCC       307
Ser Leu Val Cys Val Ser Val Ala Thr Glu Arg Ala Leu Gln Thr Pro
     55                  60                  65

ACC AAC TCC TTC ATC GTG AGC CTG GCG GCC GCC GAC CTC CTC CTC GCT       355
Thr Asn Ser Phe Ile Val Ser Leu Ala Ala Ala Asp Leu Leu Leu Ala
         70                  75                  80

CTC CTG GTG CTG CCG CTC TTC GTC TAC TCC GAG                           388
Leu Leu Val Leu Pro Leu Phe Val Tyr Ser Glu
 85                  90                  95
```

(2) INFORMATION FOR SEQ ID NO:2:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Asn Arg Ser Thr Ala Asp Ala Asp Gly Leu Leu Ala Gly Arg
  1               5                  10                  15

Gly Arg Ala Ala Gly Ala Ser Ala Gly Ala Ser Ala Gly Leu Ala Gly
             20                  25                  30

Gln Gly Ala Ala Ala Leu Val Gly Gly Val Leu Leu Ile Gly Ala Val
         35                  40                  45

Leu Ala Gly Asn Ser Leu Val Cys Val Ser Val Ala Thr Glu Arg Ala
     50                  55                  60
```

```
Leu Gln Thr Pro Thr Asn Ser Phe Ile Val Ser Leu Ala Ala Ala Asp
 65                  70                  75                  80

Leu Leu Leu Ala Leu Leu Val Leu Pro Leu Phe Val Tyr Ser Glu
                 85                  90                  95
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 1..20
        (C) IDENTIFICATION METHOD: experimental
        (D) OTHER INFORMATION: /partial
            /cons_splice= (5'site: YES, 3'site: NO)
            /evidence= EXPERIMENTAL
            /label= IntronI
            /note= "This is the 5' sequence of an intron
            estimated to be 2.0 kilobases in length"

(xi) SEQUENCE DESCRIPTION: SEQ ID NO:3:

GTGAGCCGCG TCCGGCCGCA                                        20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 1..20
        (C) IDENTIFICATION METHOD: experimental
        (D) OTHER INFORMATION: /partial
            /cons_splice= (5'site: NO, 3'site: YES)
            /evidence= EXPERIMENTAL
            /label= IntronI
            /note= "This is the 3' sequence of a intron
            estimated to be 2.0 kilobases in length."

(xi) SEQUENCE DESCRIPTION: SEQ ID NO:4:

CCTGTGGTGT CGCCGCGCAG                                        20

(2) INFORMATION FOR SEQ ID NO:5:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..113

(ix) FEATURE:
        (A) NAME/KEY: CDS
        (B) LOCATION: 1..113

(xi) SEQUENCE DESCRIPTION: SEQ ID NO:5:

```
GTC CAG GGT GGC GCG TGG CTG CTG AGC CCC CGC CTG TGC GAC GCC CTC        48
Val Gln Gly Gly Ala Trp Leu Leu Ser Pro Arg Leu Cys Asp Ala Leu
 1               5                  10                  15

ATG GCC ATG GAC GTC ATG CTG TGC ACC GCC TCC ATC TTC AAC CTG TGC        96
Met Ala Met Asp Val Met Leu Cys Thr Ala Ser Ile Phe Asn Leu Cys
                20                  25                  30

GCC ATC AGC GTG GAC AG                                                113
Ala Ile Ser Val Asp
        35
```

(2) INFORMATION FOR SEQ ID NO:6:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:6:

```
Val Gln Gly Gly Ala Trp Leu Leu Ser Pro Arg Leu Cys Asp Ala Leu
 1               5                  10                  15

Met Ala Met Asp Val Met Leu Cys Thr Ala Ser Ile Phe Asn Leu Cys
                20                  25                  30

Ala Ile Ser Val Asp
        35
```

(2) INFORMATION FOR SEQ ID NO:7:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 1..102
        (C) IDENTIFICATION METHOD: experimental
        (D) OTHER INFORMATION: /evidence= EXPERIMENTAL
            /label= IntronII (xi) SEQUENCE DESCRIPTION: SEQ ID NO:7:

```
GTGCGCCGCC CTCCCCGCCC GCGCCCCGGC GCCCCCGCGC CCCGCCCGCC GCCCTCACCG        60

CGGCCTGTGC GCTGTCCGGC GCCCCCTCGG CGCTCCCCGC AG                         102
```

(2) INFORMATION FOR SEQ ID NO:8:

(i) SEQUENCE CHARACTERISTICS:
        (A) LENGTH: 563 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..563
        (C) IDENTIFICATION METHOD: experimental
        (D) OTHER INFORMATION: /evidence= EXPERIMENTAL
            /standard_name= "Alternate Exon 3: D4.2"
            /note= "This sequence represent the sequence of
            the third exon of allele D4.2 of the human D4
            dopamine receptor gene"

(ix) FEATURE:

(A) NAME/KEY: misc_feature
                    (B) LOCATION: 257..262
                    (C) IDENTIFICATION METHOD: experimental
                    (D) OTHER INFORMATION: /function= "Polymorphic PstI site"
                        /evidence= EXPERIMENTAL
                        /label= PstI
                        /note= "This feature is the site of one of the
                        restriction enzymes whereby digestion of genomic
                        DNA produces a RFLP "

(ix) FEATURE:
                    (A) NAME/KEY: repeat_region
                    (B) LOCATION: 346..442
                    (D) OTHER INFORMATION: /rpt_type= "tandem"
                        /rpt_unit= 348 .. 396
                        /note= "This sequence represents one of 7 known
                        alleles of human D4 dopamine receptor gene
                        encoding a 16 amino acid sequence repeated twice (ix) FEATURE:
                    (A) NAME/KEY: CDS
                    (B) LOCATION: 2..563

(xi) SEQUENCE DESCRIPTION: SEQ ID NO:8:

```
G TTC GTG GCC GTG GCC GTG CCG CTG CGC TAC AAC CGG CAG GGT GGG        46
  Phe Val Ala Val Ala Val Pro Leu Arg Tyr Asn Arg Gln Gly Gly
   1               5                  10                  15

AGC CGC CGG CAG CTG CTG CTC ATC GGC GCC ACG TGG CTG CTG TCC GCG     94
Ser Arg Arg Gln Leu Leu Leu Ile Gly Ala Thr Trp Leu Leu Ser Ala
                 20                  25                  30

GCG GTG GCG GCG CCC GTA CTG TGC GGC CTC AAC GAC GTG CGC GGC CGC    142
Ala Val Ala Ala Pro Val Leu Cys Gly Leu Asn Asp Val Arg Gly Arg
             35                  40                  45

GAC CCC GCC GTG TGC CGC CTG GAG GAC CGC GAC TAC GTG GTC TAC TCG    190
Asp Pro Ala Val Cys Arg Leu Glu Asp Arg Asp Tyr Val Val Tyr Ser
         50                  55                  60

TCC GTG TGC TCC TTC TTC CTA CCC TGC CCG CTC ATG CTG CTG CTG TAC    238
Ser Val Cys Ser Phe Phe Leu Pro Cys Pro Leu Met Leu Leu Leu Tyr
     65                  70                  75

TGG GCC ACG TTC CGC GGC CTG CAG CGC TGG GAG GTG GCA CGT CGC GCC    286
Trp Ala Thr Phe Arg Gly Leu Gln Arg Trp Glu Val Ala Arg Arg Ala
 80                  85                  90                  95

AAG CTG CAC GGC CGC GCG CCC CGC CGA CCC AGC GGC CCT GGC CCG CCT    334
Lys Leu His Gly Arg Ala Pro Arg Arg Pro Ser Gly Pro Gly Pro Pro
                100                 105                 110

TCC CCC ACG CCA CCC GCG CCC CGC CTC CCC CAG GAC CCC TGC GGC CCC    382
Ser Pro Thr Pro Pro Ala Pro Arg Leu Pro Gln Asp Pro Cys Gly Pro
            115                 120                 125

GAC TGT GCG CCC CCC GCG CCC GGC CTC CCC CCG GAC CCC TGC GGC TCC    430
Asp Cys Ala Pro Pro Ala Pro Gly Leu Pro Pro Asp Pro Cys Gly Ser
        130                 135                 140

AAC TGT GCT CCC CCC GAC GCC GTC AGA GCC GCC GCG CTC CCA CCC CAG    478
Asn Cys Ala Pro Pro Asp Ala Val Arg Ala Ala Ala Leu Pro Pro Gln
    145                 150                 155

ACT CCA CCG CAG ACC CGC AGG AGG CGG CGT GCC AAG ATC ACC GGC CGG    526
Thr Pro Pro Gln Thr Arg Arg Arg Arg Ala Lys Ile Thr Gly Arg
160                 165                 170                 175

GAG CGC AAG GCC ATG AGG GTC CTG CCG GTG GTG GTC G                  563
Glu Arg Lys Ala Met Arg Val Leu Pro Val Val Val
                180                 185
```

(2) INFORMATION FOR SEQ ID NO:9:

(i) SEQUENCE CHARACTERISTICS:
            (A) LENGTH: 187 amino acids
            (B) TYPE: amino acid (D) TOPOLOGY: linear (ii) MOLECULE TYPE: protein (xi) SEQUENCE DESCRIPTION: SEQ ID NO:9:

Phe Val Ala Val Ala Val Pro Leu Arg Tyr Asn Arg Gln Gly Gly Ser
  1               5                  10                  15

Arg Arg Gln Leu Leu Leu Ile Gly Ala Thr Trp Leu Leu Ser Ala Ala
             20                  25                  30

Val Ala Ala Pro Val Leu Cys Gly Leu Asn Asp Val Arg Gly Arg Asp
         35                  40                  45

Pro Ala Val Cys Arg Leu Glu Asp Arg Asp Tyr Val Val Tyr Ser Ser
     50                  55                  60

Val Cys Ser Phe Phe Leu Pro Cys Pro Leu Met Leu Leu Leu Tyr Trp
 65                  70                  75                  80

Ala Thr Phe Arg Gly Leu Gln Arg Trp Glu Val Ala Arg Arg Ala Lys
                 85                  90                  95

Leu His Gly Arg Ala Pro Arg Arg Pro Ser Gly Pro Gly Pro Pro Ser
            100                 105                 110

Pro Thr Pro Pro Ala Pro Arg Leu Pro Gln Asp Pro Cys Gly Pro Asp
            115                 120                 125

Cys Ala Pro Pro Ala Pro Gly Leu Pro Pro Asp Pro Cys Gly Ser Asn
130                 135                 140

Cys Ala Pro Pro Asp Ala Val Arg Ala Ala Ala Leu Pro Pro Gln Thr
145                 150                 155                 160

Pro Pro Gln Thr Arg Arg Arg Arg Ala Lys Ile Thr Gly Arg Glu
                165                 170                 175

Arg Lys Ala Met Arg Val Leu Pro Val Val Val
            180                 185

(2) INFORMATION FOR SEQ ID NO:10:

(i) SEQUENCE CHARACTERISTICS:
        (A) LENGTH: 659 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..659
        (C) IDENTIFICATION METHOD: experimental
        (D) OTHER INFORMATION: /evidence= EXPERIMENTAL
            /standard_name= "Alternate Exon 3: D4.4"
            /note= "This sequence represents the third exon of
            allele D4.4 of the human D4 dopamine receptor
            gene"

(ix) FEATURE:
        (A) NAME/KEY: misc_feature
        (B) LOCATION: 257..262
        (C) IDENTIFICATION METHOD: experimental
        (D) OTHER INFORMATION: /function= "PstI site"
            /evidence= EXPERIMENTAL
            /standard_name= "PstI site"
            /label= PstI
            /note= "This sequence represents a polymorphic
            PstI site whereby digestion of human genomic DNA
            produces a RFLP "

(ix) FEATURE:
        (A) NAME/KEY: repeat_region
        (B) LOCATION: 346..538
        (C) IDENTIFICATION METHOD: experimental (D) OTHER INFORMATION: /rpt_type= "tandem"
            /evidence= EXPERIMENTAL
            /rpt_unit= 348 .. 396
            /note= "This repeat is present in 7 known alleles
            of the human D4 dopamine receptor gene and encodes
            a 16 amino acid sequence repeated 4 times in the (ix) FEATURE:
        (A) NAME/KEY: CDS
        (B) LOCATION: 2..659

(xi) SEQUENCE DESCRIPTION: SEQ ID NO:10:

```
G TTC GTG GCC GTG GCC GTG CCG CTG CGC TAC AAC CGG CAG GGT GGG         46
  Phe Val Ala Val Ala Val Pro Leu Arg Tyr Asn Arg Gln Gly Gly
  1               5                  10                  15

AGC CGC CGG CAG CTG CTG CTC ATC GGC GCC ACG TGG CTG CTG TCC GCG       94
Ser Arg Arg Gln Leu Leu Leu Ile Gly Ala Thr Trp Leu Leu Ser Ala
                20                  25                  30

GCG GTG GCG GCG CCC GTA CTG TGC GGC CTC AAC GAC GTG CGC GGC CGC      142
Ala Val Ala Ala Pro Val Leu Cys Gly Leu Asn Asp Val Arg Gly Arg
                    35                  40                  45

GAC CCC GCC GTG TGC CGC CTG GAG GAC CGC GAC TAC GTG GTC TAC TCG      190
Asp Pro Ala Val Cys Arg Leu Glu Asp Arg Asp Tyr Val Val Tyr Ser
                        50                  55                  60

TCC GTG TGC TCC TTC TTC CTA CCC TGC CCG CTC ATG CTG CTG CTG TAC      238
Ser Val Cys Ser Phe Phe Leu Pro Cys Pro Leu Met Leu Leu Leu Tyr
65                  70                  75

TGG GCC ACG TTC CGC GGC CTG CAG CGC TGG GAG GTG GCA CGT CGC GCC      286
Trp Ala Thr Phe Arg Gly Leu Gln Arg Trp Glu Val Ala Arg Arg Ala
 80                  85                  90                  95

AAG CTG CAC GGC CGC GCG CCC CGC CGA CCC AGC GGC CCT GGC CCG CCT      334
Lys Leu His Gly Arg Ala Pro Arg Arg Pro Ser Gly Pro Gly Pro Pro
                    100                 105                 110

TCC CCC ACG CCA CCC GCG CCC CGC CTC CCC CAG GAC CCC TGC GGC CCC      382
Ser Pro Thr Pro Pro Ala Pro Arg Leu Pro Gln Asp Pro Cys Gly Pro
            115                 120                 125

GAC TGT GCG CCC CCC GCG CCC GGC CTT CCC CGG GGT CCC TGC GGC CCC      430
Asp Cys Ala Pro Pro Ala Pro Gly Leu Pro Arg Gly Pro Cys Gly Pro
        130                 135                 140

GAC TGT GCG CCC GCC GCG CCC AGC CTC CCC CAG GAC CCC TGC GGC CCC      478
Asp Cys Ala Pro Ala Ala Pro Ser Leu Pro Gln Asp Pro Cys Gly Pro
    145                 150                 155

GAC TGT GCG CCC CCC GCG CCC GGC CTC CCC CCG GAC CCC TGC GGC TCC      526
Asp Cys Ala Pro Pro Ala Pro Gly Leu Pro Pro Asp Pro Cys Gly Ser
160                 165                 170                 175

AAC TGT GCT CCC CCC GAC GCC GTC AGA GCC GCC GCG CTC CCA CCC CAG      574
Asn Cys Ala Pro Pro Asp Ala Val Arg Ala Ala Ala Leu Pro Pro Gln
                180                 185                 190

ACT CCA CCG CAG ACC CGC AGG AGG CGG CGT GCC AAG ATC ACC GGC CGG      622
Thr Pro Pro Gln Thr Arg Arg Arg Arg Arg Ala Lys Ile Thr Gly Arg
            195                 200                 205

GAG CGC AAG GCC ATG AGG GTC CTG CCG GTG GTG GTC G                    659
Glu Arg Lys Ala Met Arg Val Leu Pro Val Val Val
        210                 215
```

(2) INFORMATION FOR SEQ ID NO:11:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO:11:

```
Phe Val Ala Val Ala Val Pro Leu Arg Tyr Asn Arg Gln Gly Gly Ser
 1               5                  10                  15

Arg Arg Gln Leu Leu Leu Ile Gly Ala Thr Trp Leu Leu Ser Ala Ala
            20                  25                  30

Val Ala Ala Pro Val Leu Cys Gly Leu Asn Asp Val Arg Gly Arg Asp
            35                  40                  45

Pro Ala Val Cys Arg Leu Glu Asp Arg Asp Tyr Val Val Tyr Ser Ser
            50                  55                  60

Val Cys Ser Phe Phe Leu Pro Cys Pro Leu Met Leu Leu Leu Tyr Trp
 65                  70                  75                  80

Ala Thr Phe Arg Gly Leu Gln Arg Trp Glu Val Ala Arg Arg Ala Lys
                85                  90                  95

Leu His Gly Arg Ala Pro Arg Arg Pro Ser Gly Pro Gly Pro Pro Ser
                100                 105                 110

Pro Thr Pro Pro Ala Pro Arg Leu Pro Gln Asp Pro Cys Gly Pro Asp
            115                 120                 125

Cys Ala Pro Pro Ala Pro Gly Leu Pro Arg Gly Pro Cys Gly Pro Asp
130                 135                 140

Cys Ala Pro Ala Ala Pro Ser Leu Pro Gln Asp Pro Cys Gly Pro Asp
145                 150                 155                 160

Cys Ala Pro Pro Ala Pro Gly Leu Pro Asp Pro Cys Gly Ser Asn
                165                 170                 175

Cys Ala Pro Pro Asp Ala Val Arg Ala Ala Ala Leu Pro Pro Gln Thr
            180                 185                 190

Pro Pro Gln Thr Arg Arg Arg Arg Ala Lys Ile Thr Gly Arg Glu
            195                 200                 205

Arg Lys Ala Met Arg Val Leu Pro Val Val Val
210                 215
```

(2) INFORMATION FOR SEQ ID NO:12:

(i) SEQUENCE CHARACTERISTICS:
  (A) LENGTH: 803 base pairs
  (B) TYPE: nucleic acid
  (C) STRANDEDNESS: single
  (D) TOPOLOGY: linear (ii) MOLECULE TYPE: DNA (genomic)

(ix) FEATURE:
  (A) NAME/KEY: exon
  (B) LOCATION: 1..803
  (C) IDENTIFICATION METHOD: experimental
  (D) OTHER INFORMATION: /evidence= EXPERIMENTAL
      /standard_name= "Alternate Exon 3: D4.7"
      /note= "This sequence represents the third exon of
      allele D4.7 of the human D4 dopamine receptor
      gene"

(ix) FEATURE:
  (A) NAME/KEY: misc_feature
  (B) LOCATION: 257..262
  (C) IDENTIFICATION METHOD: experimental
  (D) OTHER INFORMATION: /function= "PstI site"
      /evidence= EXPERIMENTAL
      /standard_name= "PstI site"
      /label= PstI
      /note= "This sequence is a PstI site whereby
      digestion of human genomic DNA produces a RFLP"

(ix) FEATURE:
  (A) NAME/KEY: repeat_region
  (B) LOCATION: 346..682

(C) IDENTIFICATION METHOD: experimental
(D) OTHER INFORMATION: /rpt_type= "tandem"
    /evidence= EXPERIMENTAL
    /rpt_unit= 346 .. 394
    /note= "This sequence is a repeat found in 7 known
    alleles of the human D4 dopamine receptor gene
    encoding a 16 amino acid sequence repeated 7 times (ix) FEATURE:
    (A) NAME/KEY: CDS
    (B) LOCATION: 2..803

(xi) SEQUENCE DESCRIPTION: SEQ ID NO:12:

```
G TTC GTG GCC GTG GCC GTG CCG CTG CGC TAC AAC CGG CAG GGT GGG             46
  Phe Val Ala Val Ala Val Pro Leu Arg Tyr Asn Arg Gln Gly Gly
   1               5                  10                  15

AGC CGC CGG CAG CTG CTG CTC ATC GGC GCC ACG TGG CTG CTG TCC GCG           94
Ser Arg Arg Gln Leu Leu Leu Ile Gly Ala Thr Trp Leu Leu Ser Ala
                 20                  25                  30

GCG GTG GCG GCG CCC GTA CTG TGC GGC CTC AAC GAC GTG CGC GGC CGC          142
Ala Val Ala Ala Pro Val Leu Cys Gly Leu Asn Asp Val Arg Gly Arg
                 35                  40                  45

GAC CCC GCC GTG TGC CGC CTG GAG GAC CGC GAC TAC GTG GTC TAC TCG          190
Asp Pro Ala Val Cys Arg Leu Glu Asp Arg Asp Tyr Val Val Tyr Ser
             50                  55                  60

TCC GTG TGC TCC TTC TTC CTA CCC TGC CCG CTC ATG CTG CTG CTG TAC          238
Ser Val Cys Ser Phe Phe Leu Pro Cys Pro Leu Met Leu Leu Leu Tyr
 65                  70                  75

TGG GCC ACG TTC CGC GGC CTG CAG CGC TGG GAG GTG GCA CGT CGC GCC          286
Trp Ala Thr Phe Arg Gly Leu Gln Arg Trp Glu Val Ala Arg Arg Ala
 80                  85                  90                  95

AAG CTG CAC GGC CGC GCG CCC CGC CGA CCC AGC GGC CCT GGC CCG CCT          334
Lys Leu His Gly Arg Ala Pro Arg Arg Pro Ser Gly Pro Gly Pro Pro
                100                 105                 110

TCC CCC ACG CCA CCC GCG CCC CGC CTC CCC CAG GAC CCC TGC GGC CCC          382
Ser Pro Thr Pro Pro Ala Pro Arg Leu Pro Gln Asp Pro Cys Gly Pro
                115                 120                 125

GAC TGT GCG CCC CCC GCG CCC GGC CTT CCC CGG GGT CCC TGC GGC CCC          430
Asp Cys Ala Pro Pro Ala Pro Gly Leu Pro Arg Gly Pro Cys Gly Pro
            130                 135                 140

GAC TGT GCG CCC GCC GCG CCC GGC CTC CCC CCG GAC CCC TGC GGC CCC          478
Asp Cys Ala Pro Ala Ala Pro Gly Leu Pro Pro Asp Pro Cys Gly Pro
145                 150                 155

GAC TGT GCG CCC CCC GCG CCC GGC CTC CCC CAG GAC CCC TGC GGC CCC          526
Asp Cys Ala Pro Pro Ala Pro Gly Leu Pro Gln Asp Pro Cys Gly Pro
160                 165                 170                 175

GAC TGT GCG CCC CCC GCG CCC GGC CTT CCC CGG GGT CCC TGC GGC CCC          574
Asp Cys Ala Pro Pro Ala Pro Gly Leu Pro Arg Gly Pro Cys Gly Pro
                180                 185                 190

GAC TGT GCG CCC CCC GCG CCC GGC CTC CCC CAG GAC CCC TGC GGC CCC          622
Asp Cys Ala Pro Pro Ala Pro Gly Leu Pro Gln Asp Pro Cys Gly Pro
                195                 200                 205

GAC TGT GCG CCC CCC GCG CCC GGC CTC CCC CCG GAC CCC TGC GGC TCC          670
Asp Cys Ala Pro Pro Ala Pro Gly Leu Pro Pro Asp Pro Cys Gly Ser
            210                 215                 220

AAC TGT GCT CCC CCC GAC GCC GTC AGA GCC GCC GCG CTC CCA CCC CAG          718
Asn Cys Ala Pro Pro Asp Ala Val Arg Ala Ala Ala Leu Pro Pro Gln
225                 230                 235

ACT CCA CCG CAG ACC CGC AGG AGG CGG CGT GCC AAG ATC ACC GGC CGG          766
Thr Pro Pro Gln Thr Arg Arg Arg Arg Arg Ala Lys Ile Thr Gly Arg
240                 245                 250                 255

GAG CGC AAG GCC ATG AGG GTC CTG CCG GTG GTG GTC G                        803
Glu Arg Lys Ala Met Arg Val Leu Pro Val Val Val
```

```
Glu Arg Lys Ala Met Arg Val Leu Pro Val Val Val
            260                 265
```

(2) INFORMATION FOR SEQ ID NO:13:

(i) SEQUENCE CHARACTERISTICS:
        (A) LENGTH: 267 amino acids
        (B) TYPE: amino acid
        (D) TOPOLOGY: linear (ii) MOLECULE TYPE: protein (xi) SEQUENCE DESCRIPTION: SEQ ID NO:13:

```
Phe Val Ala Val Ala Val Pro Leu Arg Tyr Asn Arg Gln Gly Gly Ser
 1               5                  10                  15

Arg Arg Gln Leu Leu Leu Ile Gly Ala Thr Trp Leu Leu Ser Ala Ala
            20                  25                  30

Val Ala Ala Pro Val Leu Cys Gly Leu Asn Asp Val Arg Gly Arg Asp
            35                  40                  45

Pro Ala Val Cys Arg Leu Glu Asp Arg Asp Tyr Val Val Tyr Ser Ser
            50                  55                  60

Val Cys Ser Phe Phe Leu Pro Cys Pro Leu Met Leu Leu Leu Tyr Trp
 65                  70                  75                  80

Ala Thr Phe Arg Gly Leu Gln Arg Trp Glu Val Ala Arg Arg Ala Lys
                 85                  90                  95

Leu His Gly Arg Ala Pro Arg Arg Pro Ser Gly Pro Gly Pro Pro Ser
            100                 105                 110

Pro Thr Pro Pro Ala Pro Arg Leu Pro Gln Asp Pro Cys Gly Pro Asp
            115                 120                 125

Cys Ala Pro Pro Ala Pro Gly Leu Pro Arg Gly Pro Cys Gly Pro Asp
            130                 135                 140

Cys Ala Pro Ala Ala Pro Gly Leu Pro Asp Pro Cys Gly Pro Asp
145                 150                 155                 160

Cys Ala Pro Pro Ala Pro Gly Leu Pro Gln Asp Pro Cys Gly Pro Asp
            165                 170                 175

Cys Ala Pro Pro Ala Pro Gly Leu Pro Arg Gly Pro Cys Gly Pro Asp
            180                 185                 190

Cys Ala Pro Pro Ala Pro Gly Leu Pro Gln Asp Pro Cys Gly Pro Asp
            195                 200                 205

Cys Ala Pro Pro Ala Pro Gly Leu Pro Pro Asp Pro Cys Gly Ser Asn
            210                 215                 220

Cys Ala Pro Pro Asp Ala Val Arg Ala Ala Leu Pro Pro Gln Thr
225                 230                 235                 240

Pro Pro Gln Thr Arg Arg Arg Arg Ala Lys Ile Thr Gly Arg Glu
            245                 250                 255

Arg Lys Ala Met Arg Val Leu Pro Val Val Val
            260                 265
```

(2) INFORMATION FOR SEQ ID NO:14:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron (B) LOCATION: 1..94

(xi) SEQUENCE DESCRIPTION: SEQ ID NO:14:

GTGGGTTCCT GTCCTGAGGG GCGGGGAGGA GAGGAGGGGG GGAGTACGAG GCCGGCTGGG        60

CGGGGGGCGC TAACGCGGCT CTCGGCGCCC CCAG        94

(2) INFORMATION FOR SEQ ID NO:15:

(i) SEQUENCE CHARACTERISTICS:
        (A) LENGTH: 328 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: exon
        (B) LOCATION: 1..328

(ix) FEATURE:
        (A) NAME/KEY: CDS
        (B) LOCATION: 3..203

(ix) FEATURE:
        (A) NAME/KEY: 3'UTR
        (B) LOCATION: 204..328

(ix) FEATURE:
        (A) NAME/KEY: polyA_site
        (B) LOCATION: 304

(ix) FEATURE:
        (A) NAME/KEY: misc_feature
        (B) LOCATION: 36..41
        (C) IDENTIFICATION METHOD: experimental
        (D) OTHER INFORMATION: /function= "HinCII site"
            /evidence= EXPERIMENTAL
            /standard_name= "HinCII site"
            /label= HinCII
            /note= "This sequence is a HinCII site whereby
            digestion of genomic DNA produces a RFLP"

(xi) SEQUENCE DESCRIPTION: SEQ ID NO:15:

```
GG GCC TTC CTG CTG TGC TGG ACG CCC TTC TTC GTG GTG CAC ATC ACG        47
   Ala Phe Leu Leu Cys Trp Thr Pro Phe Phe Val Val His Ile Thr
    1               5                  10                  15

CAG GCG CTG TGT CCT GCC TGC TCC GTG CCC CCG CGG CTG GTC AGC GCC        95
Gln Ala Leu Cys Pro Ala Cys Ser Val Pro Pro Arg Leu Val Ser Ala
                20                  25                  30

GTC ACC TGG CTG GGC TAC GTC AAC AGC GCC CTC ACC CCC GTC ATC TAC       143
Val Thr Trp Leu Gly Tyr Val Asn Ser Ala Leu Thr Pro Val Ile Tyr
            35                  40                  45

ACT GTC TTC AAC GCC GAG TTC CGC AAC GTC TTC CGC AAG GCC CTG CGT       191
Thr Val Phe Asn Ala Glu Phe Arg Asn Val Phe Arg Lys Ala Leu Arg
        50                  55                  60

GCC TGC TGC TGAGCCGGGC ACCCCCGGAC GCCCCCCGGC CTGATGGCCA                240
Ala Cys Cys
        65
```

GGCCTCAGGG ACCAAGGAGA TGGGGAGGGC GCTTTTGTAC GTTAATTAAA CAAATTCCTT       300

CCCAAACTCA GCTGTGAAGG CTCCTGGG        328

(2) INFORMATION FOR SEQ ID NO:16:

(i) SEQUENCE CHARACTERISTICS:
        (A) LENGTH: 66 amino acids
        (B) TYPE: amino acid
        (D) TOPOLOGY: linear (ii) MOLECULE TYPE: protein (xi) SEQUENCE DESCRIPTION: SEQ ID NO:16:

```
Ala Phe Leu Leu Cys Trp Thr Pro Phe Val Val His Ile Thr Gln
 1               5                  10                  15

Ala Leu Cys Pro Ala Cys Ser Val Pro Pro Arg Leu Val Ser Ala Val
                20                  25                  30

Thr Trp Leu Gly Tyr Val Asn Ser Ala Leu Thr Pro Val Ile Tyr Thr
            35                  40                  45

Val Phe Asn Ala Glu Phe Arg Asn Val Phe Arg Lys Ala Leu Arg Ala
     50                  55                  60

Cys Cys
65
```

(2) INFORMATION FOR SEQ ID NO:17:

(i) SEQUENCE CHARACTERISTICS:
        (A) LENGTH: 1370 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..103

(ix) FEATURE:
        (A) NAME/KEY: 3'UTR
        (B) LOCATION: 1268..1370

(ix) FEATURE:
        (A) NAME/KEY: CDS
        (B) LOCATION: 104..1267

(xi) SEQUENCE DESCRIPTION: SEQ ID NO:17:

```
CGGGGGCGGG ACCAGGGTCC GGCCGGGGCG TGCCCCCGGG GAGGGACTCC CCGGCTTGCC      60

CCCCGGCGTT GTCCGCGGTG CTCAGCGCCC GCCCGGGCGC GCC ATG GGG AAC CGC      115
                                             Met Gly Asn Arg
                                               1

AGC ACC GCG GAC GCG GAC GGG CTG CTG GCT GGG CGC GGG CGG GCC GCG      163
Ser Thr Ala Asp Ala Asp Gly Leu Leu Ala Gly Arg Gly Arg Ala Ala
 5              10                  15                  20

GGG GCA TCT GCG GGG GCA TCT GCG GGG CTG GCT GGG CAG GGC GCG GCG      211
Gly Ala Ser Ala Gly Ala Ser Ala Gly Leu Ala Gly Gln Gly Ala Ala
                25                  30                  35

GCG CTG GTG GGG GGC GTG CTG CTC ATC GGC GCG GTG CTC GCG GGG AAC      259
Ala Leu Val Gly Gly Val Leu Leu Ile Gly Ala Val Leu Ala Gly Asn
            40                  45                  50

TCG CTC GTG TGC GTG AGC GTG GCC ACC GAG CGC GCC CTG CAG ACG CCC      307
Ser Leu Val Cys Val Ser Val Ala Thr Glu Arg Ala Leu Gln Thr Pro
        55                  60                  65

ACC AAC TCC TTC ATC GTG AGC CTG GCG GCC GCC GAC CTC CTC CTC GCT      355
Thr Asn Ser Phe Ile Val Ser Leu Ala Ala Ala Asp Leu Leu Leu Ala
    70                  75                  80

CTC CTG GTG CTG CCG CTC TTC GTC TAC TCC GAG GTC CAG GGT GGC GCG      403
Leu Leu Val Leu Pro Leu Phe Val Tyr Ser Glu Val Gln Gly Gly Ala
85                  90                  95                 100

TGG CTG CTG AGC CCC CGC CTG TGC GAC GCC CTC ATG GCC ATG GAC GTC      451
Trp Leu Leu Ser Pro Arg Leu Cys Asp Ala Leu Met Ala Met Asp Val
                105                 110                 115
```

```
ATG CTG TGC ACC GCC TCC ATC TTC AAC CTG TGC GCC ATC AGC GTG GAC      499
Met Leu Cys Thr Ala Ser Ile Phe Asn Leu Cys Ala Ile Ser Val Asp
            120                 125                 130

AGG TTC GTG GCC GTG GCC GTG CCG CTG CGC TAC AAC CGG CAG GGT GGG      547
Arg Phe Val Ala Val Ala Val Pro Leu Arg Tyr Asn Arg Gln Gly Gly
            135                 140                 145

AGC CGC CGG CAG CTG CTC ATC GGC GCC ACG TGG CTG CTG TCC GCG          595
Ser Arg Arg Gln Leu Leu Leu Ile Gly Ala Thr Trp Leu Leu Ser Ala
    150                 155                 160

GCG GTG GCG GCG CCC GTA CTG TGC GGC CTC AAC GAC GTG CGC GGC CGC      643
Ala Val Ala Ala Pro Val Leu Cys Gly Leu Asn Asp Val Arg Gly Arg
165                 170                 175                 180

GAC CCC GCC GTG TGC CGC CTG GAG GAC CGC GAC TAC GTG GTC TAC TCG      691
Asp Pro Ala Val Cys Arg Leu Glu Asp Arg Asp Tyr Val Val Tyr Ser
                185                 190                 195

TCC GTG TGC TCC TTC TTC CTA CCC TGC CCG CTC ATG CTG CTG CTG TAC      739
Ser Val Cys Ser Phe Phe Leu Pro Cys Pro Leu Met Leu Leu Leu Tyr
            200                 205                 210

TGG GCC ACG TTC CGC GGC CTG CAG CGC TGG GAG GTG GCA CGT CGC GCC      787
Trp Ala Thr Phe Arg Gly Leu Gln Arg Trp Glu Val Ala Arg Arg Ala
            215                 220                 225

AAG CTG CAC GGC CGC GCG CCC CGC CGA CCC AGC GGC CCT GGC CCG CCT      835
Lys Leu His Gly Arg Ala Pro Arg Arg Pro Ser Gly Pro Gly Pro Pro
    230                 235                 240

TCC CCC ACG CCA CCC GCG CCC CGC CTC CCC CAG GAC CCC TGC GGC CCC      883
Ser Pro Thr Pro Pro Ala Pro Arg Leu Pro Gln Asp Pro Cys Gly Pro
245                 250                 255                 260

GAC TGT GCG CCC CCC GCG CCC GGC CTC CCC CCG GAC CCC TGC GGC TCC      931
Asp Cys Ala Pro Pro Ala Pro Gly Leu Pro Pro Asp Pro Cys Gly Ser
                265                 270                 275

AAC TGT GCT CCC CCC GAC GCC GTC AGA GCC GCC GCG CTC CCA CCC CAG      979
Asn Cys Ala Pro Pro Asp Ala Val Arg Ala Ala Ala Leu Pro Pro Gln
            280                 285                 290

ACT CCA CCG CAG ACC CGC AGG AGG CGG CGT GCC AAG ATC ACC GGC CGG     1027
Thr Pro Pro Gln Thr Arg Arg Arg Arg Arg Ala Lys Ile Thr Gly Arg
            295                 300                 305

GAG CGC AAG GCC ATG AGG GTC CTG CCG GTG GTG GTC GGG GCC TTC CTG     1075
Glu Arg Lys Ala Met Arg Val Leu Pro Val Val Val Gly Ala Phe Leu
    310                 315                 320

CTG TGC TGG ACG CCC TTC TTC GTG GTG CAC ATC ACG CAG GCG CTG TGT     1123
Leu Cys Trp Thr Pro Phe Phe Val Val His Ile Thr Gln Ala Leu Cys
325                 330                 335                 340

CCT GCC TGC TCC GTG CCC CCG CGG CTG GTC AGC GCC GTC ACC TGG CTG     1171
Pro Ala Cys Ser Val Pro Pro Arg Leu Val Ser Ala Val Thr Trp Leu
                345                 350                 355

GGC TAC GTC AAC AGC GCC CTC ACC CCC GTC ATC TAC ACT GTC TTC AAC     1219
Gly Tyr Val Asn Ser Ala Leu Thr Pro Val Ile Tyr Thr Val Phe Asn
            360                 365                 370

GCC GAG TTC CGC AAC GTC TTC CGC AAG GCC CTG CGT GCC TGC TGC TGAGCCGG 1274
Ala Glu Phe Arg Asn Val Phe Arg Lys Ala Leu Arg Ala Cys Cys
            375                 380                 385

ACCCCCGGAC GCCCCCCGGC CTGATGGCCA GGCCTCAGGG ACCAAGGAGA TGGGGAGGGC    1334

GCTTTTGTAC GTTAATTAAA CAAATTCCTT CCCAAA                              1370

(2) INFORMATION FOR SEQ ID NO:18:

(i) SEQUENCE CHARACTERISTICS:
        (A) LENGTH: 387 amino acids
        (B) TYPE: amino acid
        (D) TOPOLOGY: linear
```

(ii) MOLECULE TYPE: protein (xi) SEQUENCE DESCRIPTION: SEQ ID NO:18:

```
Met Gly Asn Arg Ser Thr Ala Asp Ala Asp Gly Leu Leu Ala Gly Arg
 1               5                  10                  15

Gly Arg Ala Ala Gly Ala Ser Ala Gly Ala Ser Ala Gly Leu Ala Gly
            20                  25                  30

Gln Gly Ala Ala Ala Leu Val Gly Gly Val Leu Leu Ile Gly Ala Val
        35                  40                  45

Leu Ala Gly Asn Ser Leu Val Cys Val Ser Val Ala Thr Glu Arg Ala
    50                  55                  60

Leu Gln Thr Pro Thr Asn Ser Phe Ile Val Ser Leu Ala Ala Ala Asp
65                  70                  75                  80

Leu Leu Leu Ala Leu Leu Val Leu Pro Leu Phe Val Tyr Ser Glu Val
                85                  90                  95

Gln Gly Gly Ala Trp Leu Leu Ser Pro Arg Leu Cys Asp Ala Leu Met
            100                 105                 110

Ala Met Asp Val Met Leu Cys Thr Ala Ser Ile Phe Asn Leu Cys Ala
        115                 120                 125

Ile Ser Val Asp Arg Phe Val Ala Val Ala Val Pro Leu Arg Tyr Asn
130                 135                 140

Arg Gln Gly Gly Ser Arg Arg Gln Leu Leu Leu Ile Gly Ala Thr Trp
145                 150                 155                 160

Leu Leu Ser Ala Ala Val Ala Ala Pro Val Leu Cys Gly Leu Asn Asp
                165                 170                 175

Val Arg Gly Arg Asp Pro Ala Val Cys Arg Leu Glu Asp Arg Asp Tyr
            180                 185                 190

Val Val Tyr Ser Ser Val Cys Ser Phe Phe Leu Pro Cys Pro Leu Met
        195                 200                 205

Leu Leu Leu Tyr Trp Ala Thr Phe Arg Gly Leu Gln Arg Trp Glu Val
210                 215                 220

Ala Arg Arg Ala Lys Leu His Gly Arg Ala Pro Arg Pro Ser Gly
225                 230                 235                 240

Pro Gly Pro Pro Ser Pro Thr Pro Pro Ala Pro Arg Leu Pro Gln Asp
                245                 250                 255

Pro Cys Gly Pro Asp Cys Ala Pro Pro Ala Pro Gly Leu Pro Pro Asp
            260                 265                 270

Pro Cys Gly Ser Asn Cys Ala Pro Pro Asp Ala Val Arg Ala Ala Ala
        275                 280                 285

Leu Pro Pro Gln Thr Pro Pro Gln Thr Arg Arg Arg Arg Arg Ala Lys
    290                 295                 300

Ile Thr Gly Arg Glu Arg Lys Ala Met Arg Val Leu Pro Val Val Val
305                 310                 315                 320

Gly Ala Phe Leu Leu Cys Trp Thr Pro Phe Phe Val Val His Ile Thr
                325                 330                 335

Gln Ala Leu Cys Pro Ala Cys Ser Val Pro Pro Arg Leu Val Ser Ala
            340                 345                 350

Val Thr Trp Leu Gly Tyr Val Asn Ser Ala Leu Thr Pro Val Ile Tyr
        355                 360                 365

Thr Val Phe Asn Ala Glu Phe Arg Asn Val Phe Arg Lys Ala Leu Arg
    370                 375                 380

Ala Cys Cys
385
```

(2) INFORMATION FOR SEQ ID NO:19:

(i) SEQUENCE CHARACTERISTICS:
        (A) LENGTH: 1466 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..103

(ix) FEATURE:
        (A) NAME/KEY: 3'UTR
        (B) LOCATION: 1364..1466

(ix) FEATURE:
        (A) NAME/KEY: CDS
        (B) LOCATION: 104..1363

(xi) SEQUENCE DESCRIPTION: SEQ ID NO:19:

```
CGGGGGCGGG ACCAGGGTCC GGCCGGGGCG TGCCCCCGGG GAGGGACTCC CCGGCTTGCC        60

CCCCGGCGTT GTCCGCGGTG CTCAGCGCCC GCCCGGGCGC GCC ATG GGG AAC CGC        115
                                                Met Gly Asn Arg
                                                 1

AGC ACC GCG GAC GCG GAC GGG CTG CTG GCT GGG CGC GGG CGG GCC GCG        163
Ser Thr Ala Asp Ala Asp Gly Leu Leu Ala Gly Arg Gly Arg Ala Ala
 5                  10                  15                  20

GGG GCA TCT GCG GGG GCA TCT GCG GGG CTG GCT GGG CAG GGC GCG GCG        211
Gly Ala Ser Ala Gly Ala Ser Ala Gly Leu Ala Gly Gln Gly Ala Ala
                 25                  30                  35

GCG CTG GTG GGG GGC GTG CTG CTC ATC GGC GCG GTG CTC GCG GGG AAC        259
Ala Leu Val Gly Gly Val Leu Leu Ile Gly Ala Val Leu Ala Gly Asn
         40                  45                  50

TCG CTC GTG TGC GTG AGC GTG GCC ACC GAG CGC GCC CTG CAG ACG CCC        307
Ser Leu Val Cys Val Ser Val Ala Thr Glu Arg Ala Leu Gln Thr Pro
 55                  60                  65

ACC AAC TCC TTC ATC GTG AGC CTG GCG GCC GCC GAC CTC CTC CTC GCT        355
Thr Asn Ser Phe Ile Val Ser Leu Ala Ala Ala Asp Leu Leu Leu Ala
     70                  75                  80

CTC CTG GTG CTG CCG CTC TTC GTC TAC TCC GAG GTC CAG GGT GGC GCG        403
Leu Leu Val Leu Pro Leu Phe Val Tyr Ser Glu Val Gln Gly Gly Ala
 85                  90                  95                 100

TGG CTG CTG AGC CCC CGC CTG TGC GAC GCC CTC ATG GCC ATG GAC GTC        451
Trp Leu Leu Ser Pro Arg Leu Cys Asp Ala Leu Met Ala Met Asp Val
                105                 110                 115

ATG CTG TGC ACC GCC TCC ATC TTC AAC CTG TGC GCC ATC AGC GTG GAC        499
Met Leu Cys Thr Ala Ser Ile Phe Asn Leu Cys Ala Ile Ser Val Asp
        120                 125                 130

AGG TTC GTG GCC GTG GCC GTG CCG CTG CGC TAC AAC CGG CAG GGT GGG        547
Arg Phe Val Ala Val Ala Val Pro Leu Arg Tyr Asn Arg Gln Gly Gly
        135                 140                 145

AGC CGC CGG CAG CTG CTG CTC ATC GGC GCC ACG TGG CTG CTG TCC GCG        595
Ser Arg Arg Gln Leu Leu Leu Ile Gly Ala Thr Trp Leu Leu Ser Ala
        150                 155                 160

GCG GTG GCG GCG CCC GTA CTG TGC GGC CTC AAC GAC GTG CGC GGC CGC        643
Ala Val Ala Ala Pro Val Leu Cys Gly Leu Asn Asp Val Arg Gly Arg
165                 170                 175                 180

GAC CCC GCC GTG TGC CGC CTG GAG GAC CGC GAC TAC GTG GTC TAC TCG        691
Asp Pro Ala Val Cys Arg Leu Glu Asp Arg Asp Tyr Val Val Tyr Ser
                185                 190                 195
```

-continued

```
TCC GTG TGC TCC TTC TTC CTA CCC TGC CCG CTC ATG CTG CTG CTG TAC      739
Ser Val Cys Ser Phe Phe Leu Pro Cys Pro Leu Met Leu Leu Leu Tyr
            200                 205                 210

TGG GCC ACG TTC CGC GGC CTG CAG CGC TGG GAG GTG GCA CGT CGC GCC      787
Trp Ala Thr Phe Arg Gly Leu Gln Arg Trp Glu Val Ala Arg Arg Ala
                215                 220                 225

AAG CTG CAC GGC CGC GCG CCC CGC CGA CCC AGC GGC CCT GGC CCG CCT      835
Lys Leu His Gly Arg Ala Pro Arg Arg Pro Ser Gly Pro Gly Pro Pro
230                 235                 240

TCC CCC ACG CCA CCC GCG CCC CGC CTC CCC CAG GAC CCC TGC GGC CCC      883
Ser Pro Thr Pro Pro Ala Pro Arg Leu Pro Gln Asp Pro Cys Gly Pro
245                 250                 255                 260

GAC TGT GCG CCC CCC GCG CCC GGC CTT CCC CGG GGT CCC TGC GGC CCC      931
Asp Cys Ala Pro Pro Ala Pro Gly Leu Pro Arg Gly Pro Cys Gly Pro
                265                 270                 275

GAC TGT GCG CCC GCC GCG CCC AGC CTC CCC CAG GAC CCC TGC GGC CCC      979
Asp Cys Ala Pro Ala Ala Pro Ser Leu Pro Gln Asp Pro Cys Gly Pro
                280                 285                 290

GAC TGT GCG CCC CCC GCG CCC GGC CTC CCC CCG GAC CCC TGC GGC TCC     1027
Asp Cys Ala Pro Pro Ala Pro Gly Leu Pro Pro Asp Pro Cys Gly Ser
            295                 300                 305

AAC TGT GCT CCC CCC GAC GCC GTC AGA GCC GCC GCG CTC CCA CCC CAG     1075
Asn Cys Ala Pro Pro Asp Ala Val Arg Ala Ala Ala Leu Pro Pro Gln
        310                 315                 320

ACT CCA CCG CAG ACC CGC AGG AGG CGG CGT GCC AAG ATC ACC GGC CGG     1123
Thr Pro Pro Gln Thr Arg Arg Arg Arg Arg Ala Lys Ile Thr Gly Arg
325                 330                 335                 340

GAG CGC AAG GCC ATG AGG GTC CTG CCG GTG GTG GTC GGG GCC TTC CTG     1171
Glu Arg Lys Ala Met Arg Val Leu Pro Val Val Val Gly Ala Phe Leu
                345                 350                 355

CTG TGC TGG ACG CCC TTC TTC GTG GTG CAC ATC ACG CAG GCG CTG TGT     1219
Leu Cys Trp Thr Pro Phe Phe Val Val His Ile Thr Gln Ala Leu Cys
                360                 365                 370

CCT GCC TGC TCC GTG CCC CCG CGG CTG GTC AGC GCC GTC ACC TGG CTG     1267
Pro Ala Cys Ser Val Pro Pro Arg Leu Val Ser Ala Val Thr Trp Leu
            375                 380                 385

GGC TAC GTC AAC AGC GCC CTC ACC CCC GTC ATC TAC ACT GTC TTC AAC     1315
Gly Tyr Val Asn Ser Ala Leu Thr Pro Val Ile Tyr Thr Val Phe Asn
            390                 395                 400

GCC GAG TTC CGC AAC GTC TTC CGC AAG GCC CTG CGT GCC TGC TGC TGAGCCGG1370
Ala Glu Phe Arg Asn Val Phe Arg Lys Ala Leu Arg Ala Cys Cys
405                 410                 415                 420

ACCCCCGGAC GCCCCCCGGC CTGATGGCCA GGCCTCAGGG ACCAAGGAGA TGGGGAGGGC   1430

GCTTTTGTAC GTTAATTAAA CAAATTCCTT CCCAAA                            1466

(2) INFORMATION FOR SEQ ID NO:20:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:20:

Met Gly Asn Arg Ser Thr Ala Asp Ala Asp Gly Leu Leu Ala Gly Arg
 1               5                  10                  15

Gly Arg Ala Ala Gly Ala Ser Ala Gly Ala Ser Ala Gly Leu Ala Gly
                20                  25                  30
```

```
Gln Gly Ala Ala Ala Leu Val Gly Val Leu Leu Ile Gly Ala Val
         35                  40                  45

Leu Ala Gly Asn Ser Leu Val Cys Val Ser Val Ala Thr Glu Arg Ala
     50                  55                  60

Leu Gln Thr Pro Thr Asn Ser Phe Ile Val Ser Leu Ala Ala Ala Asp
 65                  70                  75                  80

Leu Leu Leu Ala Leu Leu Val Leu Pro Leu Phe Val Tyr Ser Glu Val
                 85                  90                  95

Gln Gly Gly Ala Trp Leu Leu Ser Pro Arg Leu Cys Asp Ala Leu Met
            100                 105                 110

Ala Met Asp Val Met Leu Cys Thr Ala Ser Ile Phe Asn Leu Cys Ala
        115                 120                 125

Ile Ser Val Asp Arg Phe Val Ala Val Ala Val Pro Leu Arg Tyr Asn
    130                 135                 140

Arg Gln Gly Gly Ser Arg Arg Gln Leu Leu Leu Ile Gly Ala Thr Trp
145                 150                 155                 160

Leu Leu Ser Ala Ala Val Ala Ala Pro Val Leu Cys Gly Leu Asn Asp
                165                 170                 175

Val Arg Gly Arg Asp Pro Ala Val Cys Arg Leu Glu Asp Arg Asp Tyr
            180                 185                 190

Val Val Tyr Ser Ser Val Cys Ser Phe Phe Leu Pro Cys Pro Leu Met
        195                 200                 205

Leu Leu Leu Tyr Trp Ala Thr Phe Arg Gly Leu Gln Arg Trp Glu Val
    210                 215                 220

Ala Arg Arg Ala Lys Leu His Gly Arg Ala Pro Arg Arg Pro Ser Gly
225                 230                 235                 240

Pro Gly Pro Pro Ser Pro Thr Pro Pro Ala Pro Arg Leu Pro Gln Asp
                245                 250                 255

Pro Cys Gly Pro Asp Cys Ala Pro Pro Ala Pro Gly Leu Pro Arg Gly
            260                 265                 270

Pro Cys Gly Pro Asp Cys Ala Pro Ala Ala Pro Ser Leu Pro Gln Asp
        275                 280                 285

Pro Cys Gly Pro Asp Cys Ala Pro Pro Ala Pro Gly Leu Pro Pro Asp
    290                 295                 300

Pro Cys Gly Ser Asn Cys Ala Pro Pro Asp Ala Val Arg Ala Ala Ala
305                 310                 315                 320

Leu Pro Pro Gln Thr Pro Pro Gln Thr Arg Arg Arg Arg Arg Ala Lys
                325                 330                 335

Ile Thr Gly Arg Glu Arg Lys Ala Met Arg Val Leu Pro Val Val Val
            340                 345                 350

Gly Ala Phe Leu Leu Cys Trp Thr Pro Phe Phe Val Val His Ile Thr
        355                 360                 365

Gln Ala Leu Cys Pro Ala Cys Ser Val Pro Pro Arg Leu Val Ser Ala
    370                 375                 380

Val Thr Trp Leu Gly Tyr Val Asn Ser Ala Leu Thr Pro Val Ile Tyr
385                 390                 395                 400

Thr Val Phe Asn Ala Glu Phe Arg Asn Val Phe Arg Lys Ala Leu Arg
                405                 410                 415

Ala Cys Cys (2) INFORMATION FOR SEQ ID NO:21:

(i) SEQUENCE CHARACTERISTICS:
        (A) LENGTH: 1610 base pairs
```

-continued

```
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..103

(ix) FEATURE:
        (A) NAME/KEY: 3'UTR
        (B) LOCATION: 1508..1610

(ix) FEATURE:
        (A) NAME/KEY: CDS
        (B) LOCATION: 104..1507

(xi) SEQUENCE DESCRIPTION: SEQ ID NO:21:
```

```
CGGGGGCGGG ACCAGGGTCC GGCCGGGGCG TGCCCCCGGG GAGGGACTCC CCGGCTTGCC       60

CCCCGGCGTT GTCCGCGGTG CTCAGCGCCC GCCCGGGCGC GCC ATG GGG AAC CGC       115
                                             Met Gly Asn Arg
                                               1

AGC ACC GCG GAC GCG GAC GGG CTG CTG GCT GGG CGC GGG CGG GCC GCG       163
Ser Thr Ala Asp Ala Asp Gly Leu Leu Ala Gly Arg Gly Arg Ala Ala
  5              10                  15                  20

GGG GCA TCT GCG GGG GCA TCT GCG GGG CTG GCT GGG CAG GGC GCG GCG       211
Gly Ala Ser Ala Gly Ala Ser Ala Gly Leu Ala Gly Gln Gly Ala Ala
                 25                  30                  35

GCG CTG GTG GGG GGC GTG CTC CTC ATC GGC GCG GTG CTC GCG GGG AAC       259
Ala Leu Val Gly Gly Val Leu Leu Ile Gly Ala Val Leu Ala Gly Asn
     40                  45                  50

TCG CTC GTG TGC GTG AGC GTG GCC ACC GAG CGC GCC CTG CAG ACG CCC       307
Ser Leu Val Cys Val Ser Val Ala Thr Glu Arg Ala Leu Gln Thr Pro
 55                  60                  65

ACC AAC TCC TTC ATC GTG AGC CTG GCG GCC GCC GAC CTC CTC CTC GCT       355
Thr Asn Ser Phe Ile Val Ser Leu Ala Ala Ala Asp Leu Leu Leu Ala
     70                  75                  80

CTC CTG GTG CTG CCG CTC TTC GTC TAC TCC GAG GTC CAG GGT GGC GCG       403
Leu Leu Val Leu Pro Leu Phe Val Tyr Ser Glu Val Gln Gly Gly Ala
 85                  90                  95                 100

TGG CTG CTG AGC CCC CGC CTG TGC GAC GCC CTC ATG GCC ATG GAC GTC       451
Trp Leu Leu Ser Pro Arg Leu Cys Asp Ala Leu Met Ala Met Asp Val
                105                 110                 115

ATG CTG TGC ACC GCC TCC ATC TTC AAC CTG TGC GCC ATC AGC GTG GAC       499
Met Leu Cys Thr Ala Ser Ile Phe Asn Leu Cys Ala Ile Ser Val Asp
            120                 125                 130

AGG TTC GTG GCC GTG GCC GTG CCG CTG CGC TAC AAC CGG CAG GGT GGG       547
Arg Phe Val Ala Val Ala Val Pro Leu Arg Tyr Asn Arg Gln Gly Gly
        135                 140                 145

AGC CGC CGG CAG CTG CTG CTC ATC GGC GCC ACG TGG CTG CTG TCC GCG       595
Ser Arg Arg Gln Leu Leu Leu Ile Gly Ala Thr Trp Leu Leu Ser Ala
    150                 155                 160

GCG GTG GCG GCG CCC GTA CTG TGC GGC CTC AAC GAC GTG CGC GGC CGC       643
Ala Val Ala Ala Pro Val Leu Cys Gly Leu Asn Asp Val Arg Gly Arg
165                 170                 175                 180

GAC CCC GCC GTG TGC CGC CTG GAG GAC CGC GAC TAC GTG GTC TAC TCG       691
Asp Pro Ala Val Cys Arg Leu Glu Asp Arg Asp Tyr Val Val Tyr Ser
                185                 190                 195

TCC GTG TGC TCC TTC TTC CTA CCC TGC CCG CTC ATG CTG CTG CTG TAC       739
Ser Val Cys Ser Phe Phe Leu Pro Cys Pro Leu Met Leu Leu Leu Tyr
            200                 205                 210

TGG GCC ACG TTC CGC GGC CTG CAG CGC TGG GAG GTG GCA CGT CGC GCC       787
```

```
Trp Ala Thr Phe Arg Gly Leu Gln Arg Trp Glu Val Ala Arg Arg Ala
            215                 220                 225

AAG CTG CAC GGC CGC GCG CCC CGC CGA CCC AGC GGC CCT GGC CCG CCT      835
Lys Leu His Gly Arg Ala Pro Arg Arg Pro Ser Gly Pro Gly Pro Pro
        230                 235                 240

TCC CCC ACG CCA CCC GCG CCC CGC CTC CCC CAG GAC CCC TGC GGC CCC      883
Ser Pro Thr Pro Pro Ala Pro Arg Leu Pro Gln Asp Pro Cys Gly Pro
245                 250                 255                 260

GAC TGT GCG CCC CCC GCG CCC GGC CTT CCC CGG GGT CCC TGC GGC CCC      931
Asp Cys Ala Pro Pro Ala Pro Gly Leu Pro Arg Gly Pro Cys Gly Pro
                265                 270                 275

GAC TGT GCG CCC GCC GCG CCC GGC CTC CCC CCG GAC CCC TGC GGC CCC      979
Asp Cys Ala Pro Ala Ala Pro Gly Leu Pro Pro Asp Pro Cys Gly Pro
            280                 285                 290

GAC TGT GCG CCC CCC GCG CCC GGC CTC CCC CAG GAC CCC TGC GGC CCC     1027
Asp Cys Ala Pro Pro Ala Pro Gly Leu Pro Gln Asp Pro Cys Gly Pro
        295                 300                 305

GAC TGT GCG CCC CCC GCG CCC GGC CTT CCC CGG GGT CCC TGC GGC CCC     1075
Asp Cys Ala Pro Pro Ala Pro Gly Leu Pro Arg Gly Pro Cys Gly Pro
310                 315                 320

GAC TGT GCG CCC CCC GCG CCC GGC CTC CCC CAG GAC CCC TGC GGC CCC     1123
Asp Cys Ala Pro Pro Ala Pro Gly Leu Pro Gln Asp Pro Cys Gly Pro
325                 330                 335                 340

GAC TGT GCG CCC CCC GCG CCC GGC CTC CCC CCG GAC CCC TGC GGC TCC     1171
Asp Cys Ala Pro Pro Ala Pro Gly Leu Pro Pro Asp Pro Cys Gly Ser
                345                 350                 355

AAC TGT GCT CCC CCC GAC GCC GTC AGA GCC GCC GCG CTC CCA CCC CAG     1219
Asn Cys Ala Pro Pro Asp Ala Val Arg Ala Ala Ala Leu Pro Pro Gln
            360                 365                 370

ACT CCA CCG CAG ACC CGC AGG AGG CGG CGT GCC AAG ATC ACC GGC CGG     1267
Thr Pro Pro Gln Thr Arg Arg Arg Arg Arg Ala Lys Ile Thr Gly Arg
        375                 380                 385

GAG CGC AAG GCC ATG AGG GTC CTG CCG GTG GTG GTC GGG GCC TTC CTG     1315
Glu Arg Lys Ala Met Arg Val Leu Pro Val Val Val Gly Ala Phe Leu
        390                 395                 400

CTG TGC TGG ACG CCC TTC TTC GTG GTG CAC ATC ACG CAG GCG CTG TGT     1363
Leu Cys Trp Thr Pro Phe Phe Val Val His Ile Thr Gln Ala Leu Cys
405                 410                 415                 420

CCT GCC TGC TCC GTG CCC CCG CGG CTG GTC AGC GCC GTC ACC TGG CTG     1411
Pro Ala Cys Ser Val Pro Pro Arg Leu Val Ser Ala Val Thr Trp Leu
                425                 430                 435

GGC TAC GTC AAC AGC GCC CTC ACC CCC GTC ATC TAC ACT GTC TTC AAC     1459
Gly Tyr Val Asn Ser Ala Leu Thr Pro Val Ile Tyr Thr Val Phe Asn
            440                 445                 450

GCC GAG TTC CGC AAC GTC TTC CGC AAG GCC CTG CGT GCC TGC TGAGCCGG   1514
Ala Glu Phe Arg Asn Val Phe Arg Lys Ala Leu Arg Ala Cys Cys
        455                 460                 465

ACCCCCGGAC GCCCCCCGGC CTGATGGCCA GGCCTCAGGG ACCAAGGAGA TGGGGAGGGC   1574

GCTTTTGTAC GTTAATTAAA CAAATTCCTT CCCAAA                             1610

(2) INFORMATION FOR SEQ ID NO:22:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:22:
```

```
Met Gly Asn Arg Ser Thr Ala Asp Ala Asp Gly Leu Leu Ala Gly Arg
  1               5                  10                  15

Gly Arg Ala Ala Gly Ala Ser Ala Gly Ala Ser Ala Gly Leu Ala Gly
                 20                  25                  30

Gln Gly Ala Ala Ala Leu Val Gly Gly Val Leu Leu Ile Gly Ala Val
             35                  40                  45

Leu Ala Gly Asn Ser Leu Val Cys Val Ser Val Ala Thr Glu Arg Ala
         50                  55                  60

Leu Gln Thr Pro Thr Asn Ser Phe Ile Val Ser Leu Ala Ala Ala Asp
 65                  70                  75                  80

Leu Leu Leu Ala Leu Leu Val Leu Pro Leu Phe Val Tyr Ser Glu Val
                 85                  90                  95

Gln Gly Gly Ala Trp Leu Leu Ser Pro Arg Leu Cys Asp Ala Leu Met
             100                 105                 110

Ala Met Asp Val Met Leu Cys Thr Ala Ser Ile Phe Asn Leu Cys Ala
         115                 120                 125

Ile Ser Val Asp Arg Phe Val Ala Val Ala Val Pro Leu Arg Tyr Asn
 130                 135                 140

Arg Gln Gly Gly Ser Arg Arg Gln Leu Leu Leu Ile Gly Ala Thr Trp
145                 150                 155                 160

Leu Leu Ser Ala Ala Val Ala Ala Pro Val Leu Cys Gly Leu Asn Asp
                 165                 170                 175

Val Arg Gly Arg Asp Pro Ala Val Cys Arg Leu Glu Asp Arg Asp Tyr
             180                 185                 190

Val Val Tyr Ser Ser Val Cys Ser Phe Phe Leu Pro Cys Pro Leu Met
         195                 200                 205

Leu Leu Leu Tyr Trp Ala Thr Phe Arg Gly Leu Gln Arg Trp Glu Val
 210                 215                 220

Ala Arg Arg Ala Lys Leu His Gly Arg Ala Pro Arg Arg Pro Ser Gly
225                 230                 235                 240

Pro Gly Pro Pro Ser Pro Thr Pro Pro Ala Pro Arg Leu Pro Gln Asp
                 245                 250                 255

Pro Cys Gly Pro Asp Cys Ala Pro Pro Ala Pro Gly Leu Pro Arg Gly
             260                 265                 270

Pro Cys Gly Pro Asp Cys Ala Pro Ala Ala Pro Gly Leu Pro Pro Asp
         275                 280                 285

Pro Cys Gly Pro Asp Cys Ala Pro Pro Ala Pro Gly Leu Pro Gln Asp
 290                 295                 300

Pro Cys Gly Pro Asp Cys Ala Pro Pro Ala Pro Gly Leu Pro Arg Gly
305                 310                 315                 320

Pro Cys Gly Pro Asp Cys Ala Pro Pro Ala Pro Gly Leu Pro Gln Asp
                 325                 330                 335

Pro Cys Gly Pro Asp Cys Ala Pro Pro Ala Pro Gly Leu Pro Pro Asp
             340                 345                 350

Pro Cys Gly Ser Asn Cys Ala Pro Pro Asp Ala Val Arg Ala Ala Ala
         355                 360                 365

Leu Pro Pro Gln Thr Pro Pro Gln Thr Arg Arg Arg Arg Arg Ala Lys
 370                 375                 380

Ile Thr Gly Arg Glu Arg Lys Ala Met Arg Val Leu Pro Val Val Val
385                 390                 395                 400

Gly Ala Phe Leu Leu Cys Trp Thr Pro Phe Phe Val Val His Ile Thr
                 405                 410                 415

Gln Ala Leu Cys Pro Ala Cys Ser Val Pro Pro Arg Leu Val Ser Ala
```

```
                         420                425                430
Val Thr Trp Leu Gly Tyr Val Asn Ser Ala Leu Thr Pro Val Ile Tyr
            435                440                445

Thr Val Phe Asn Ala Glu Phe Arg Asn Val Phe Arg Lys Ala Leu Arg
    450                455                460

Ala Cys Cys
465
```

(2) INFORMATION FOR SEQ ID NO:23:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

ACCCGCGCCC CGCCTCCCCC AGGACCCCTG CGGCCCCGAC TGTGCGCC        48

(2) INFORMATION FOR SEQ ID NO:24:

(i) SEQUENCE CHARACTERISTICS:
        (A) LENGTH: 16 amino acids
        (B) TYPE: amino acid
        (D) TOPOLOGY: linear (ii) MOLECULE TYPE: protein (ix) FEATURE:
        (A) NAME/KEY: Peptide
        (B) LOCATION: 1..4
        (D) OTHER INFORMATION: /label= Variants
            /note= "X residues at position 1 may be Pro or Ala
            and at position 5 may be Arg or Gly;"

(ix) FEATURE:
        (A) NAME/KEY: Peptide
        (B) LOCATION: 7..8
        (D) OTHER INFORMATION: /label= Variants
            /note= "X residues at position 7 may be Pro or Arg
            or Gln and at position 8 may be Asp or Gly;"

(ix) FEATURE:
        (A) NAME/KEY: Peptide
        (B) LOCATION: 12..13
        (D) OTHER INFORMATION: /label= Variants
            /note= "X residues at position 12 may be Pro or Ser
            and at position 13 may be Asp or Asn;"

(xi) SEQUENCE DESCRIPTION: SEQ ID NO:24:

```
Xaa Ala Pro Xaa Leu Pro Xaa Xaa Pro Cys Gly Xaa Xaa Cys Ala Pro
 1               5              10               15
```

What is claimed is:

1. A method of screening a compound for binding to a human D4 dopamine receptor, the method comprising the following steps:

(a) transforming a host cell with a recombinant expression construct encoding a human D4 dopamine receptor having an amino acid sequence that is the amino acid sequence of the human D4 dopamine receptor allele D4.4 from amino acid 1 to amino acid 248 (SEQ ID No.: 20), covalently linked at the carboxyl terminus of amino acid 248 to the amino terminus of a repeated amino acid sequence, the carboxyl terminus of the repeated amino acid sequence being covalently linked to the amino terminus of the amino acid sequence of the human D4 dopamine receptor allele D4.4 from amino acid 312 to amino acid 419 (SEQ ID No.: 20), wherein the amino acid sequence of the repeated sequence comprises from 3 to 8 copies of the amino acid sequence:

(Pro/Ala).Ala.Pro.(Arg/Gly).Leu.Pro.(Gln/Arg/Pro).(Asp/Gly).Pro.Cys.Gly.(Pro/Ser).(Asp/Asn).Cys.Ala.Pro (SEQ ID No.:24), wherein the cells of the transformed cell culture express the receptor; and (b) assaying the transformed cell with the compound to determine whether the compound binds to the human D4 dopamine receptor.

2. The method of claim 1, wherein the human D4 dopamine receptor is selected from the group consisting of the human dopamine D4 receptor alleles identified by D4.2 (SEQ ID No.: 18), D4.4 (SEQ ID No.: 20) and D4.7 (SEQ ID No.: 22).

3. A method of screening a compound for competitive binding to a human D4 dopamine receptor, the method comprising the following steps:

(a) transforming a host cell with a recombinant expression construct encoding a human D4 dopamine receptor having an amino acid sequence that is the amino acid sequence of the human D4 dopamine receptor allele D4.4 from amino acid 1 to amino acid 248 (SEQ ID No.: 20), covalently linked at the carboxyl terminus of amino acid 248 to the amino terminus of a repeated amino acid sequence, the carboxyl terminus of the repeated amino acid sequence being covalently linked to the amino terminus of the amino acid sequence of the human D4 dopamine receptor allele D4.4 from amino acid 312 to amino acid 419 (SEQ ID No.: 20), wherein the amino acid sequence of the repeated sequence comprises from 3 to 8 copies of the amino acid sequence:

(Pro/Ala).Ala.Pro.(Arg/Gly).Leu.Pro.(Gln/Arg/Pro).(Asp/Gly).Pro.Cys.Gly.(Pro/Ser).(Asp/Asn).Cys.Ala.Pro (SEQ ID No.:24), wherein the cells of the transformed cell culture express the receptor;

(b) assaying the transformed cell with the compound in the presence and in the absence of an agonist for the human D4 dopamine receptor; and (c) determining whether the compound competes with the agonist for binding to the human D4 dopamine receptor.

4. The method of claim 3, wherein the human D4 dopamine receptor is selected from the group consisting of the human dopamine D4 receptor alleles identified by D4.2 (SEQ ID No.: 18), D4.4 (SEQ ID No.: 20) and D4.7 (SEQ ID No.: 22).

5. The method of claim 3, wherein the compound is detectably-labeled.

6. The method of claim 3, wherein the human D4 dopamine receptor agonist is detectably-labeled.

7. The method of claim 3, wherein the compound is quantitatively characterized by assaying the transformed cell culture with varying amounts of the compound in the presence of a detectably-labeled agonist for the human D4 dopamine receptor and measuring the extent of competition with binding of the detectably-labeled agonist thereby.

8. A method of screening a compound to determine if the compound is an agonist binding inhibitor of a human D4 dopamine receptor, the method comprising the following steps:

(a) transforming a host cell with a recombinant expression construct encoding a human D4 dopamine receptor having an amino acid sequence that is the amino acid sequence of the human D4 dopamine receptor allele D4.4 from amino acid 1 to amino acid 248 (SEQ ID No.: 20), covalently linked at the carboxyl terminus of amino acid 248 to the amino terminus of a repeated amino acid sequence, the carboxyl terminus of the repeated amino acid sequence being covalently linked to the amino terminus of the amino acid sequence of the human D4 dopamine receptor allele D4.4 from amino acid 312 to amino acid 419 (SEQ ID No.: 20), wherein the amino acid sequence of the repeated sequence comprises from 3 to 8 copies of the amino acid sequence:

(Pro/Ala).Ala.Pro.(Arg/Gly).Leu.Pro.(Gln/Arg/Pro).(Asp/Gly).Pro.Cys.Gly.(Pro/Ser).(Asp/Asn).Cys.Ala.Pro (SEQ ID No.:24), wherein the cells of the transformed cell culture express the receptor; and (b) assaying the transformed cell culture with the compound in the presence of a human D4 dopamine receptor agonist to determine whether the compound is capable of inhibiting agonist binding to the receptor.

9. The method of claim 8, wherein the human D4 dopamine receptor is selected from the group consisting of the human dopamine D4 receptor alleles identified by D4.2 (SEQ ID No.: 18), D4.4 (SEQ ID No.: 20) and D4.7 (SEQ ID No.: 22).

10. The method of claim 8, wherein the compound is detectably-labeled.

11. The method of claim 8, wherein the human D4 dopamine receptor agonist is detectably-labeled.

12. The method of claim 11, wherein the compound is quantitatively characterized by assaying the transformed cell culture with varying amounts of the compound in the presence of a detectably-labeled human D4 dopamine receptor agonist and measuring the extent of inhibition of detectably-labeled agonist binding thereby.

* * * * *